(12) United States Patent
Knackmuss et al.

(10) Patent No.: US 7,507,797 B2
(45) Date of Patent: Mar. 24, 2009

(54) SINGLE-CHAIN ANTIBODY ACTING AGAINST 37 KDA/67 KDA lAMININ RECEPTOR AS TOOLS FOR THE DIAGNOSIS AND THERAPY OF PRION DISEASES AND CANCER, PRODUCTION AND USE THEREOF

(75) Inventors: Stefan Knackmuss, Plankstadt (DE); Clémence Rey, München (DE); Peter Röttgen, Ladenburg (DE); Claudia Büttner, Schwetzingen (DE); Uwe Reusch, Maikammer (DE)

(73) Assignee: Affimed Therapeutics AG, Heidelberg (DE)

( * ) Notice: Subject to any disclaimer, the term of this patent is extended or adjusted under 35 U.S.C. 154(b) by 44 days.

(21) Appl. No.: 10/574,961

(22) PCT Filed: Oct. 8, 2004

(86) PCT No.: PCT/EP2004/011268

§ 371 (c)(1),
(2), (4) Date: Jul. 5, 2006

(87) PCT Pub. No.: WO2005/035580

PCT Pub. Date: Apr. 21, 2005

(65) Prior Publication Data

US 2007/0041977 A1    Feb. 22, 2007

(30) Foreign Application Priority Data

Oct. 8, 2003    (DE)    ................ 103 46 627

(51) Int. Cl.
C07K 10/00    (2006.01)
A61K 39/395    (2006.01)
C12N 15/00    (2006.01)

(52) U.S. Cl. .............. 530/387.9; 530/387.1; 530/388.2; 530/387.3; 435/69.6; 435/70.2

(58) Field of Classification Search ........................ None
See application file for complete search history.

(56) References Cited

U.S. PATENT DOCUMENTS 4,686,180 A    8/1987    Coggin, Jr. et al.

FOREIGN PATENT DOCUMENTS

EP    1 127 894 A1    8/2001
WO    WO 89/11273 A1    11/1989

OTHER PUBLICATIONS

Sanz et al. Gene Therapy, 2002, vol. 9, p. 1049-1053.*
Irani et al. Annual Reviews in Medicine, vol. 54, p. 305-319.*
Coulthart et al. (Canadian Medical Association, 2001, vol. 165, p. 51-58.*
Georgieva, Experimental Pathology and Parasitology, 2002, p. 60-63.*
Rudikoff et al. PNAS, 1982, vol. 79, p. 1979-1983.*
Panka et al. PNAS, 1988, vol. 85, p. 3080-3084.*
Lederman et al. (Molecular Immunology 28: 1171-1181, 1991.*
Li et al. (PNAS 77:3211-3214, 1980.*
Roman Rieger et al: The Human 37-kDa Laminin Receptor Precursor Interacts With The Prion Protein In Eukaryotic Cells; Nature Medicine, Nature Publishing, vol. 3, No. 12, pp. 1383-1388, XP-002094757, Dec. 1997.
Coggin, J. H. JR. et al: 37 KiloDalton Oncofetal Antigen Protein And Immature Laminin Receptor Protein Are Identical, Universal T-Cell Inducing Immunogens On Primary Rodent And Human Cancers; Anticancer Research, Helenic Anticancer Institute; Athens, Greece; Bd. 19, Nr. 6C, pp. 5535-5542, XP-002981891; Nov. 1999.
Melvyn Little et al: Generation Of A Large Complex Antibody Library From Multiple Donors; Journal of Immunological Methods, Elsevier Science Publishers B.V., Amsterdam, Netherlands, Bd. 231, Nr. 1-2, pp. 3-9, Dec. 1999.
Catherine Hutchings et al: Generation Of Naive Human Antibody Libraries; Antibody Engineering, Chapter 6, Springer Verlag Berlin; pp. 94-108, XP-002316010, 2001.
Gesundheitsforschung Des BMBF: "Vorhabenübersicht: TSE-Neurodegenerative Erkrankungen", Bekanntmachungen des Bundesministerium Fuer Bildung und Forschung, Online! 2001; pp. 1-15, XP-002316009, Feb. 2, 2005.

* cited by examiner

*Primary Examiner*—Bruce Campell
*Assistant Examiner*—Agnieszka Boesen
(74) *Attorney, Agent, or Firm*—Breiner & Breiner, LLC

(57) ABSTRACT

Single-chain antibodies are described which specifically recognize both the 37 kDa precursor form of the laminin receptor (37 kDa LRP) and the 67 kDa high-affinity form of the laminin receptor (67 kDa LR), and pharmaceutical and diagnostic compositions which contain these single-chain antibodies.

14 Claims, 27 Drawing Sheets

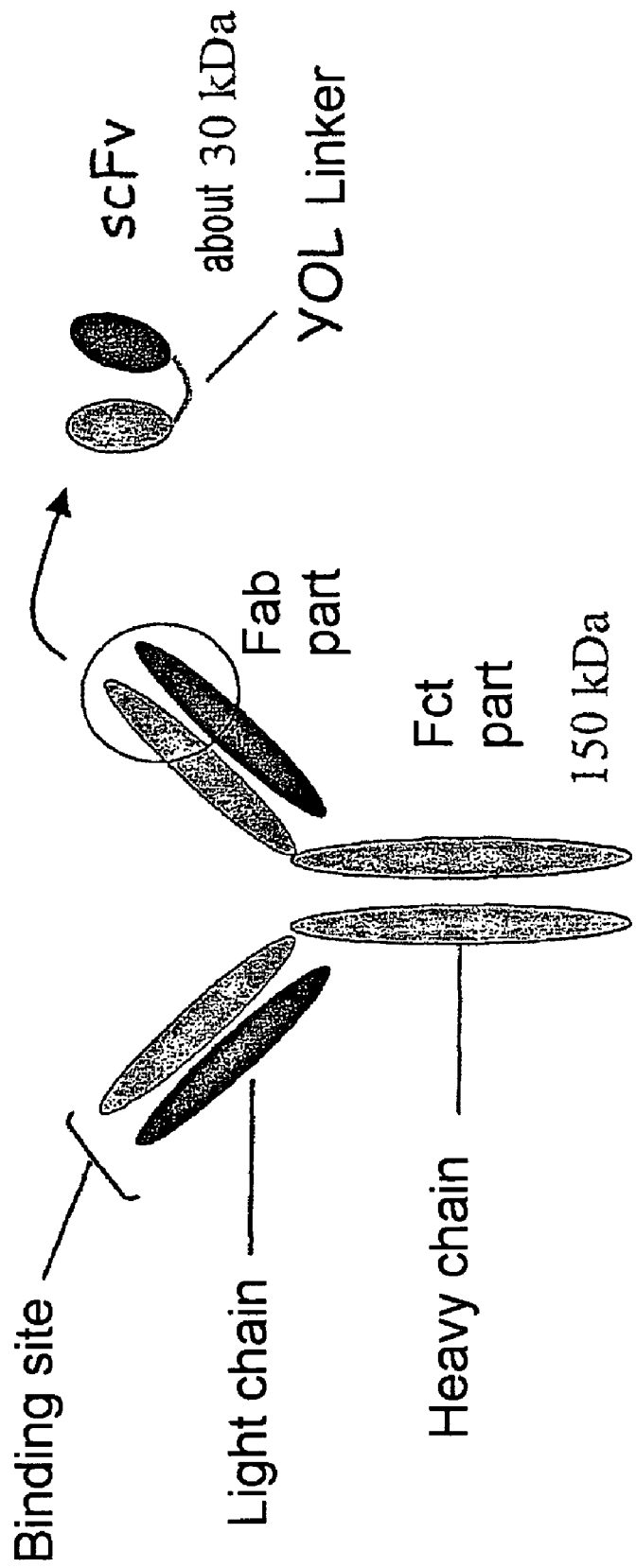
Fig. 1. Schematic representation of an scFv in comparison with the full-length antibody.

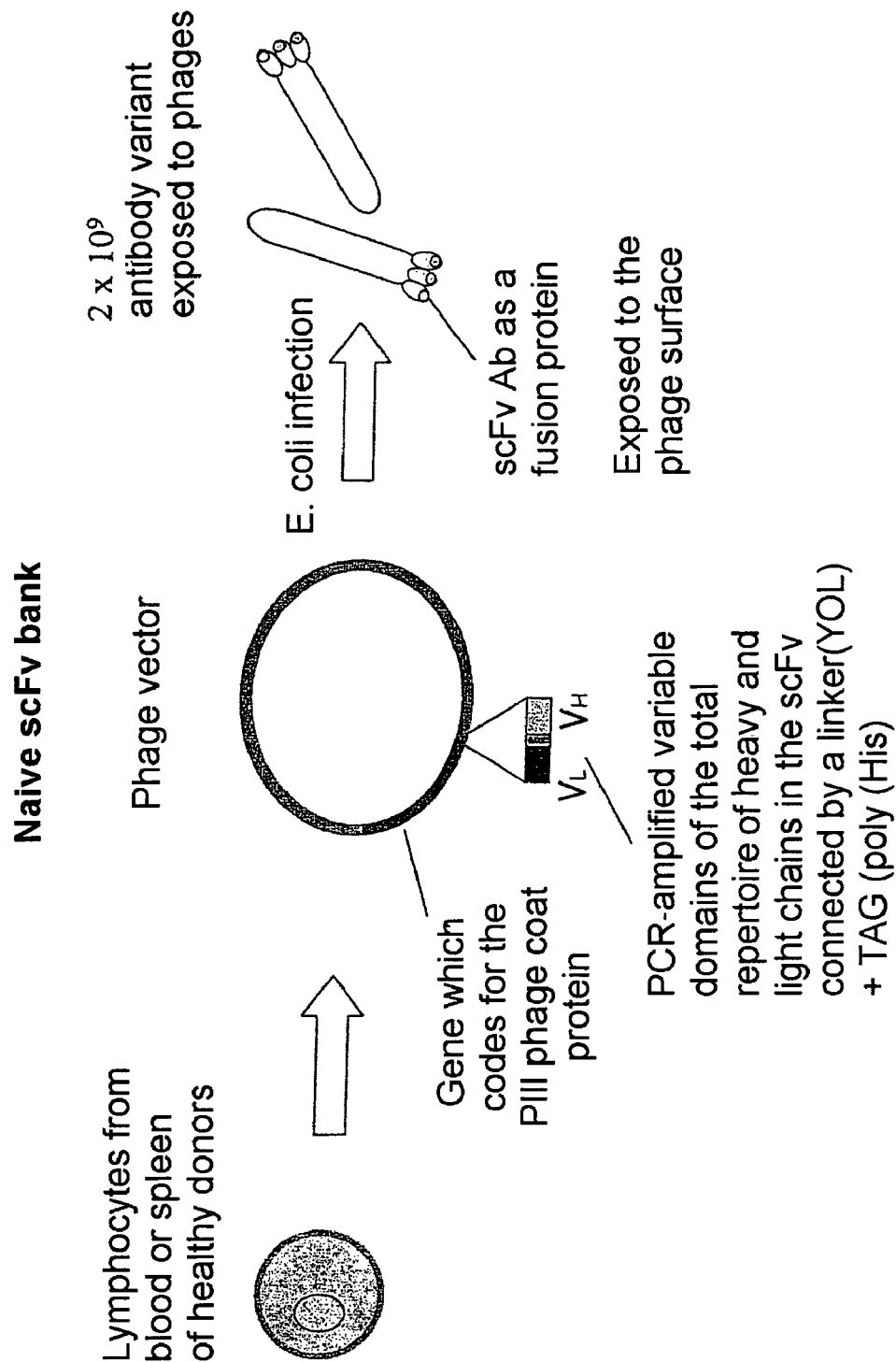
Fig. 2. Schematic representation of the generation of the naive scFv bank from lymphocytes from blood or spleen.

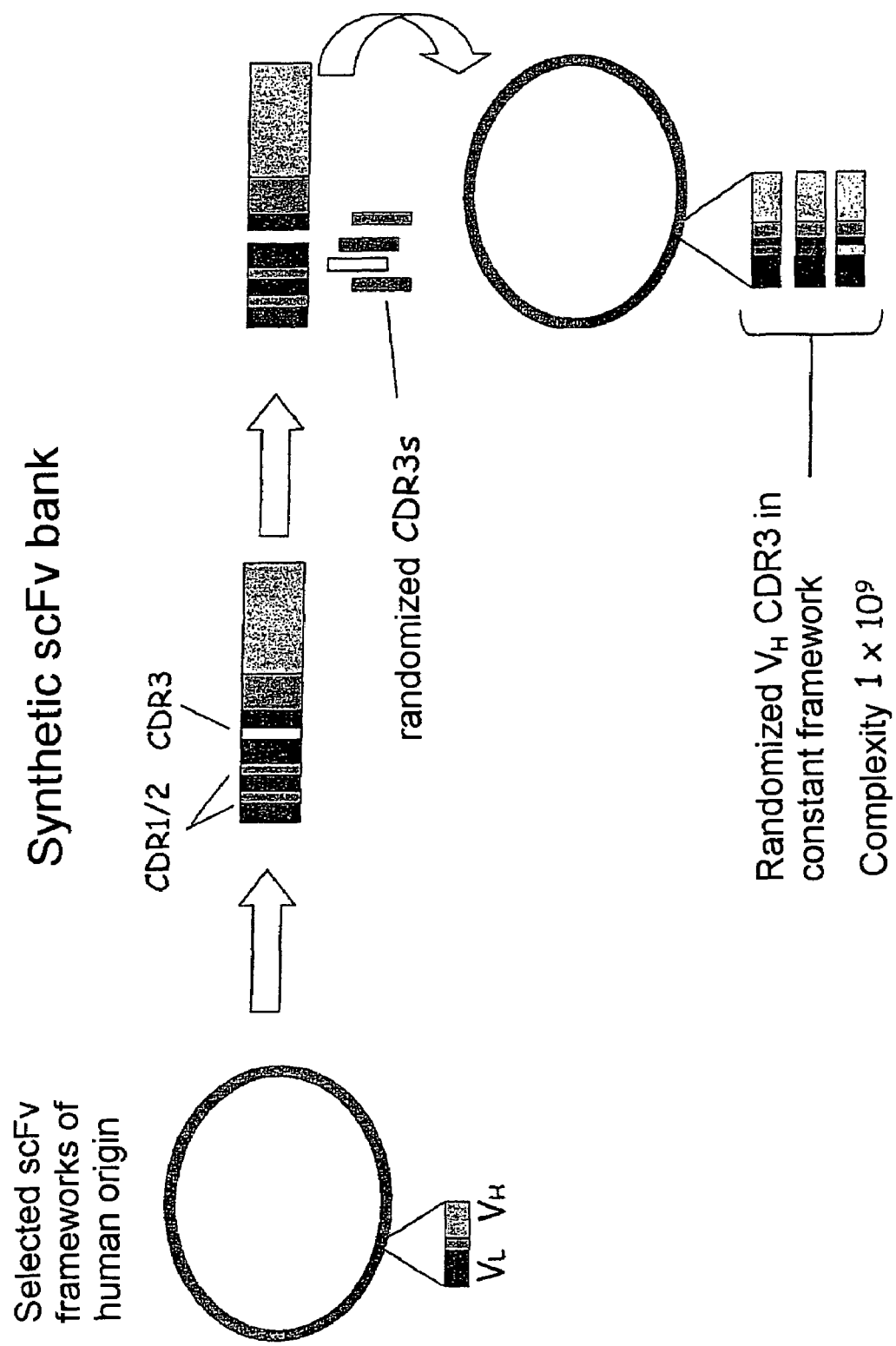
Fig. 3. Schematic representation of the synthetic scFv bank.

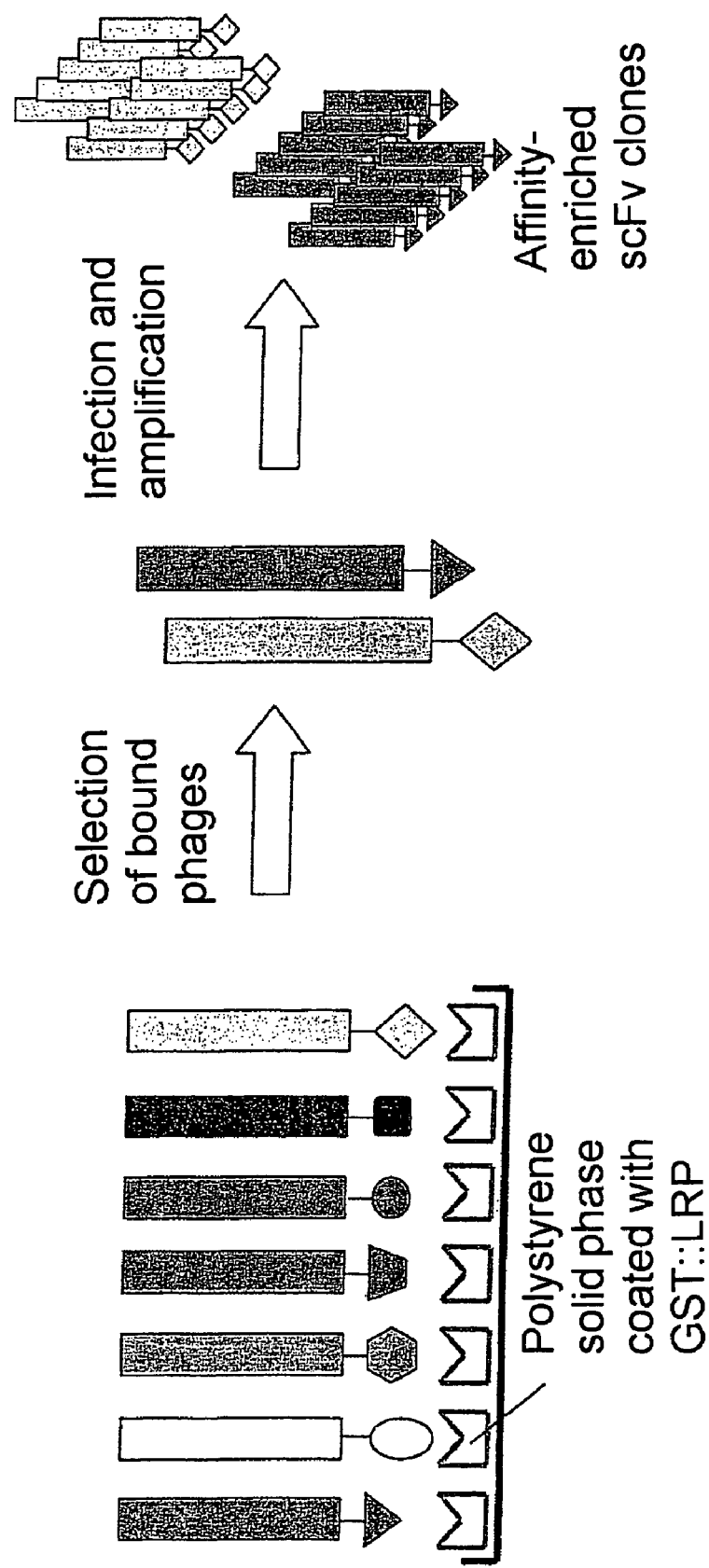
Fig. 4: Schematic representation of the screening of anti-LRP scFv antibodies against GST::LRP by "phage display" using the naive or synthetic scFv banks which are shown in Fig. 1 and Fig. 2.

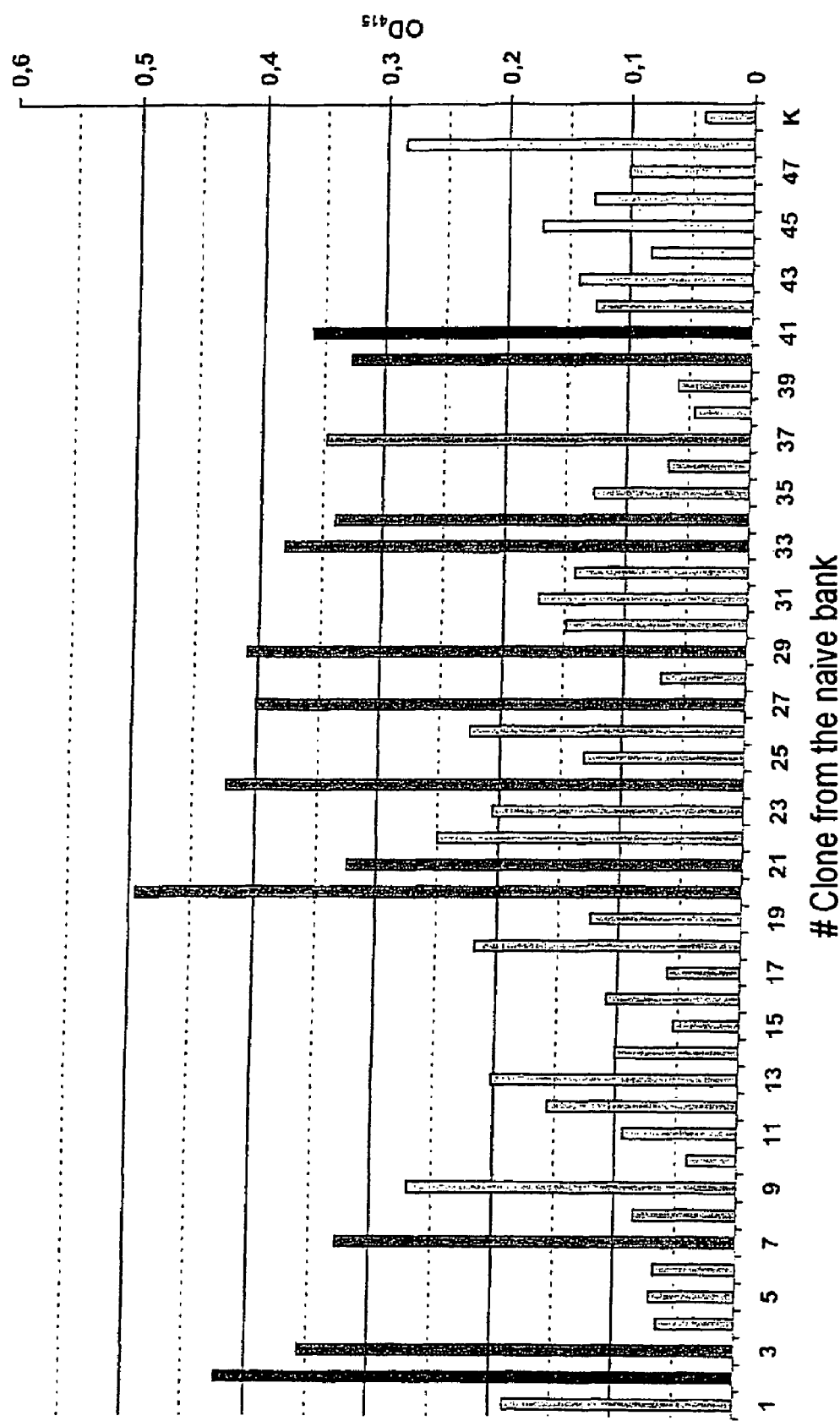
Fig. 5. ELISA of periplasmatic crude extracts of individual clones obtained after three selection rounds from the naive scFv bank

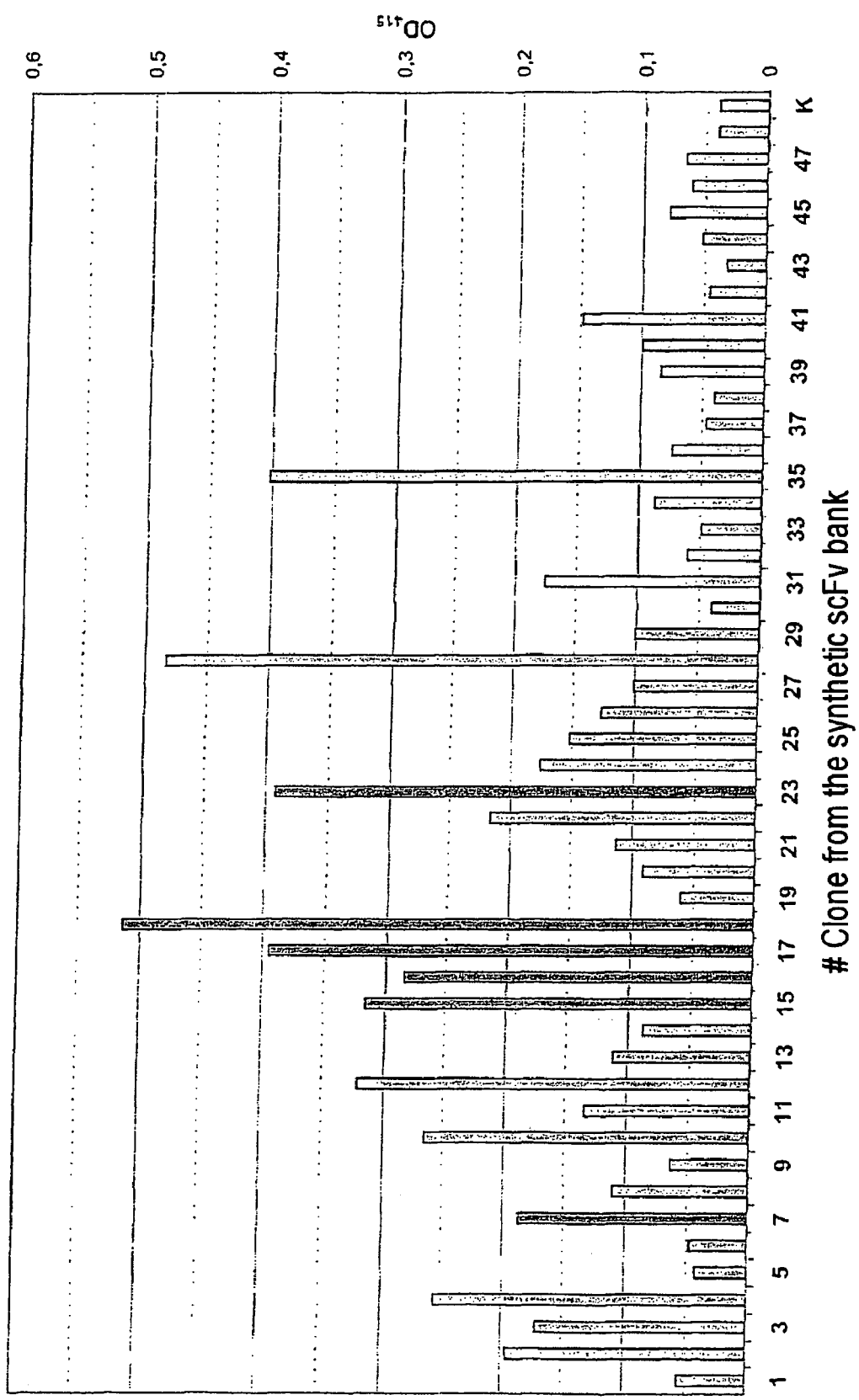
Fig. 6. ELISA of periplasmatic crude extracts of individual clones obtained from the synthetic scFv bank

- Three panning rounds on soluble GST::LRP bound directly to the solid phase
- Identification of individually positive clones in the ELISA

- for GST::LRP fusion, with αHis-HRP
- Fresh testing positively identified clones for GST to the exclusion of GST Specificity

|  | GST::LRP | GST |
|---|---|---|
| ELISA Positive N | 66% | - |
| S | 53% | - |
| Selected clones N | 13 | neg. |
| S | 6 | neg. |
| BstN I groups  N | 10/13  2/13  1/13 | - |

Fig. 7. Results of the ELISA from Figs. 5 and 6 after three selection rounds on GST::LRP fusion protein

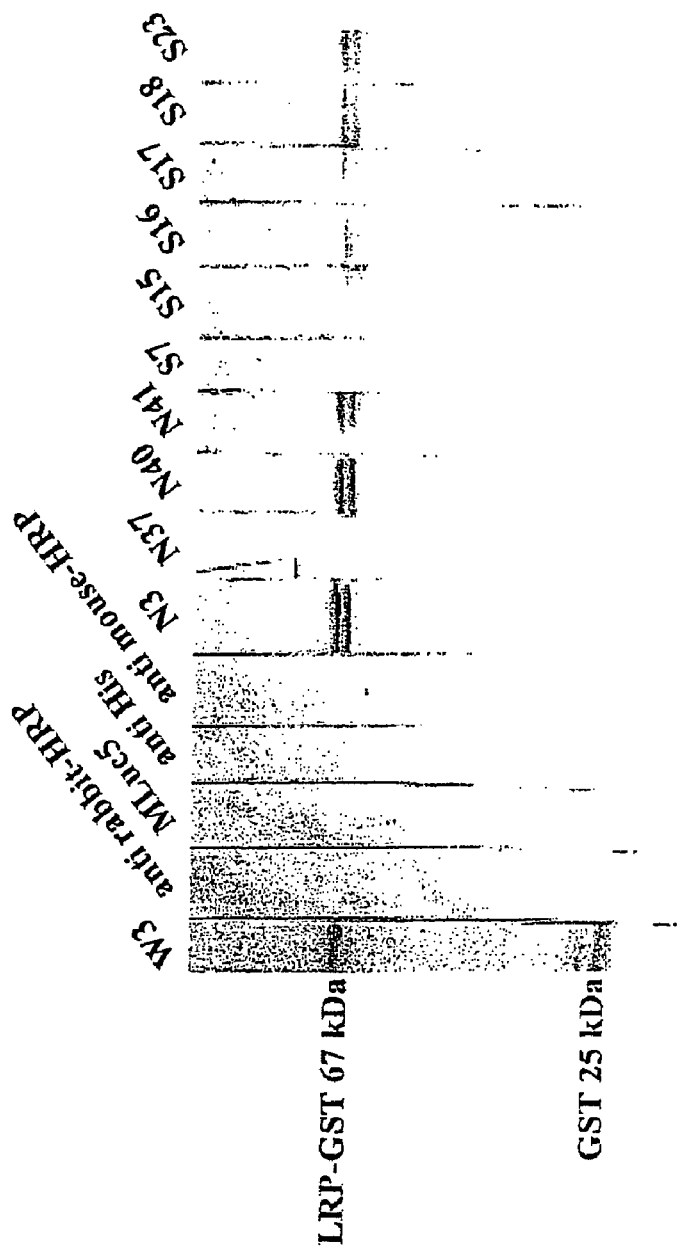
Fig. 8. Western Blot analysis of recombinant GST::LRP/GST detected using scFvs from the naive and synthetic scFv banks

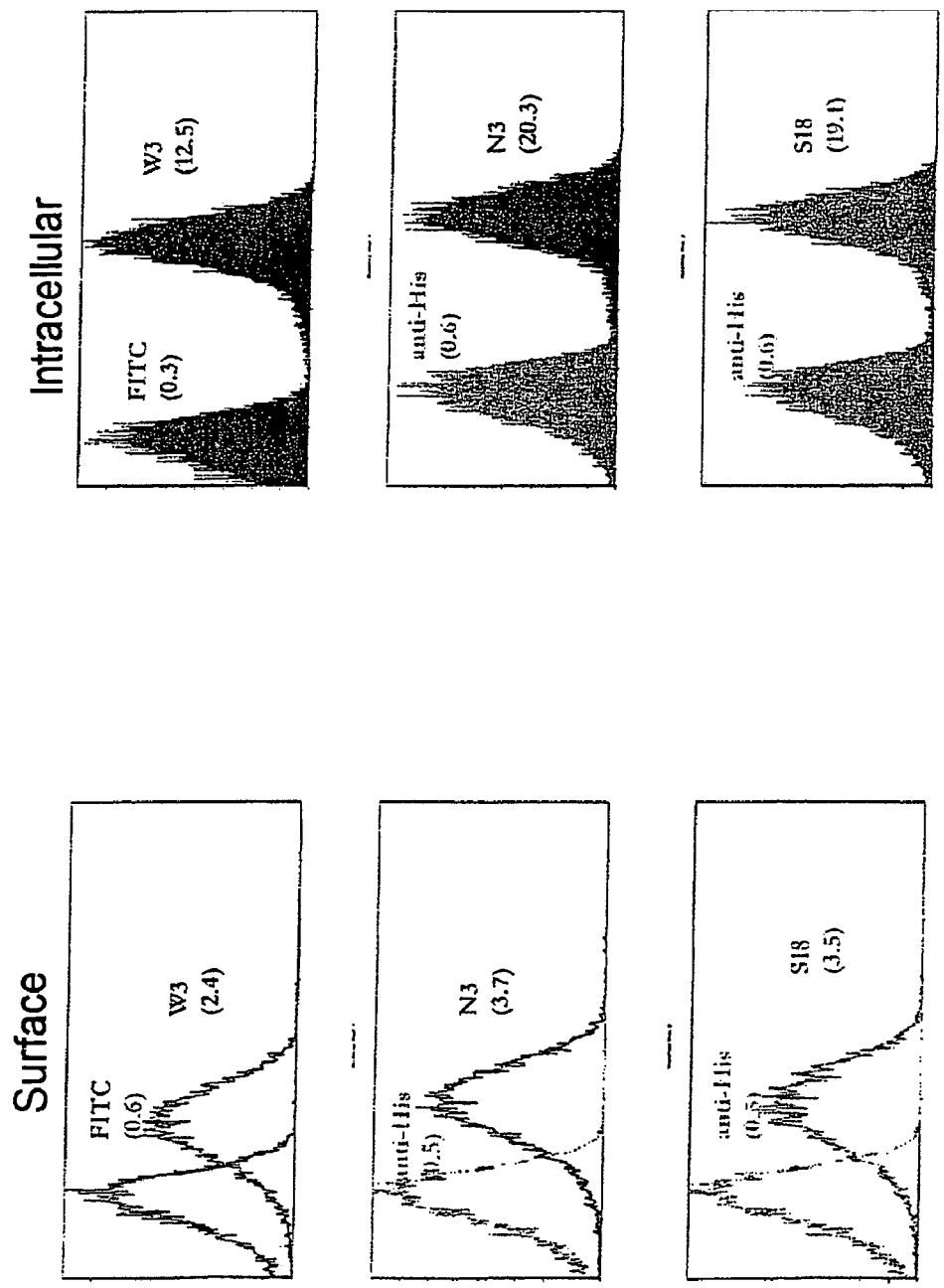
Fig. 9. The antibodies W3, S18 and N3 recognize LRP/LR in and on N2a cells

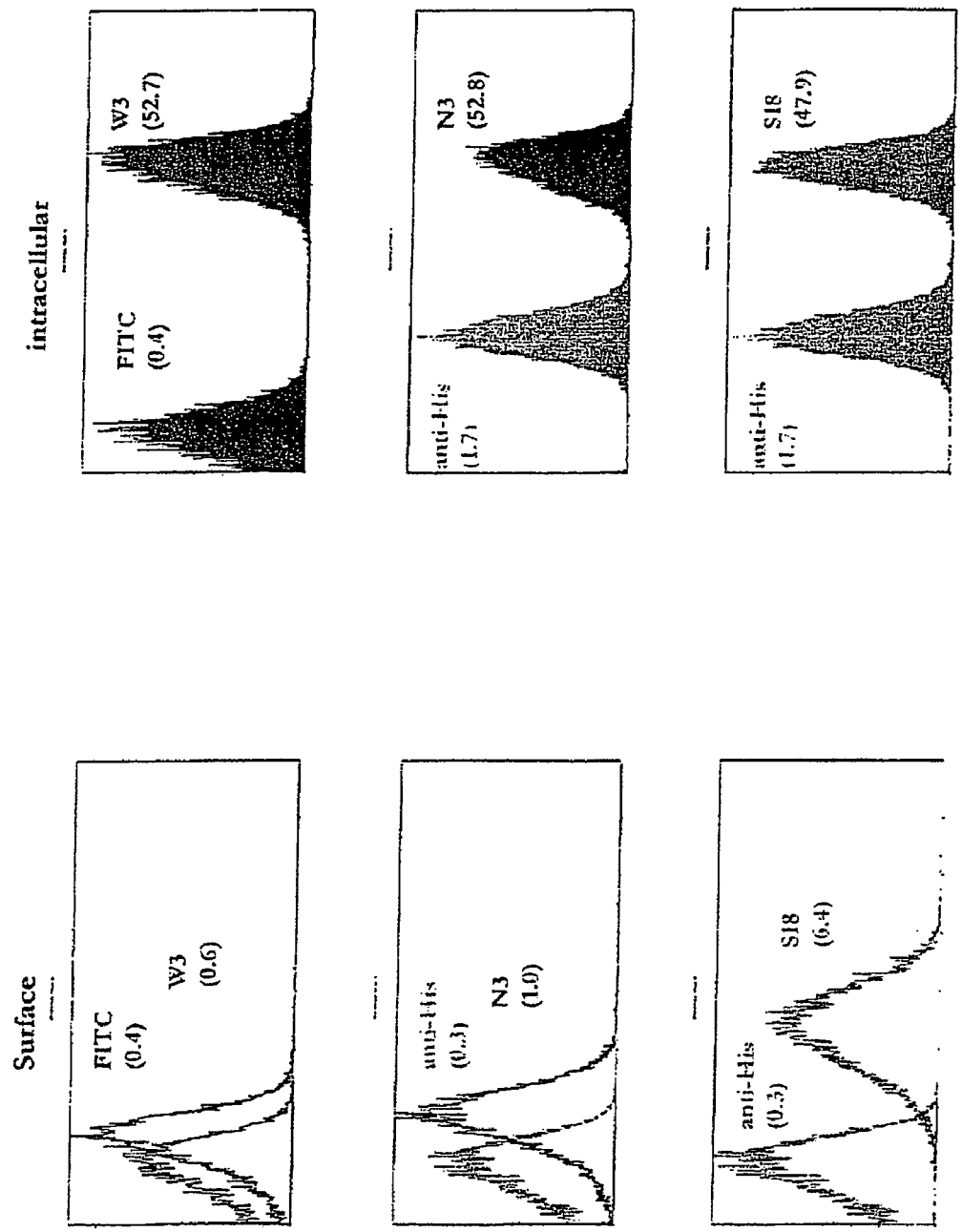
Fig. 10. The antibodies W3, S18 and N3 recognize LRP/LR in and on Jurkat cells

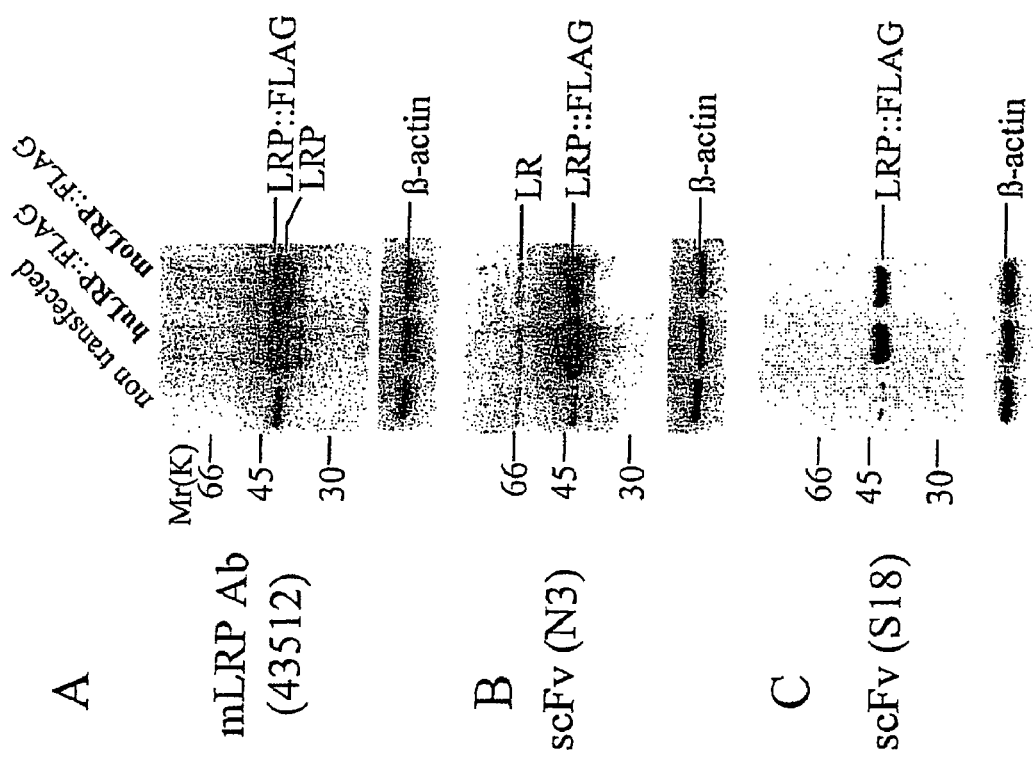
Fig. 11. Western Blot analysis of rec. LRP::FLAG and endogenous LRP/LR in BHK cells transfected with rec. Semliki forest virus RNA Fig. 12. IF analysis of rec. LRP::FLAG and endogenous LRP/LR on the surface of BHK cells transfected with rec. Semliki forest virus RNAs

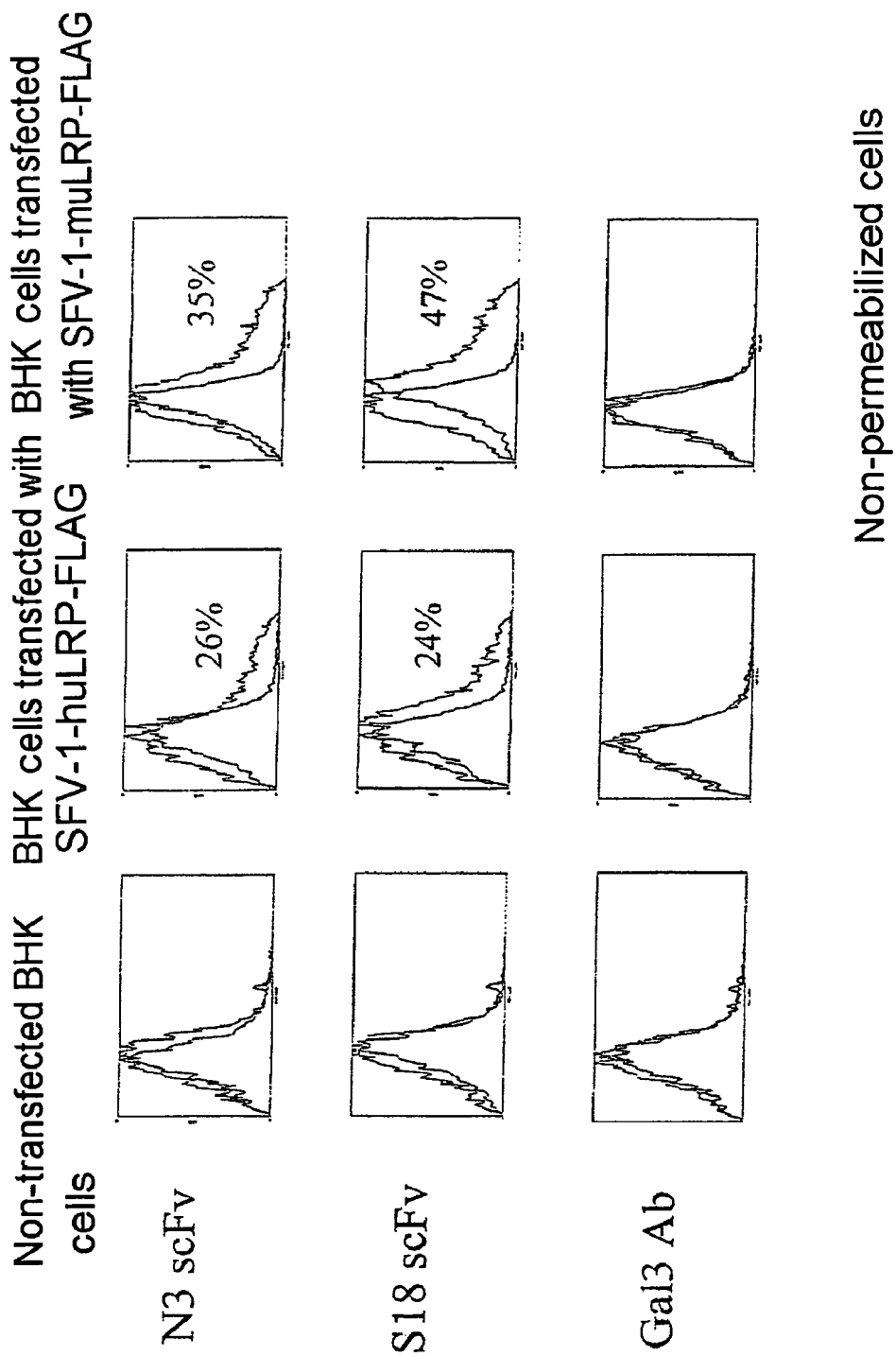
Fig. 13. FACS analysis of rec. LRP::FLAG and endogenous LRP/LR on the surface of BHK cells transfected with rec. Semliki forest virus RNAs

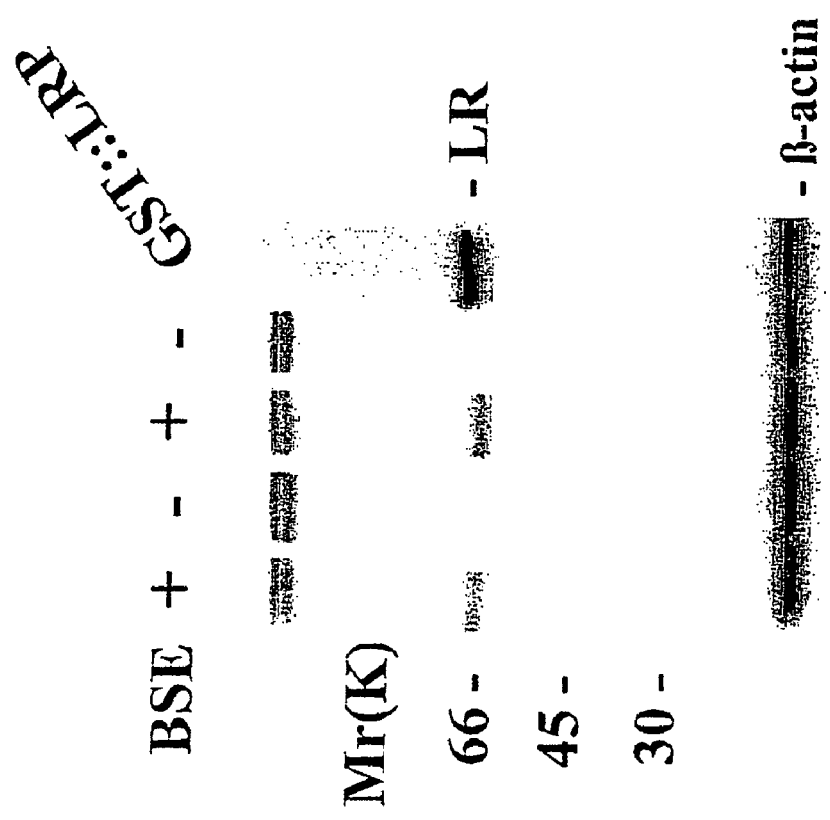
Fig. 14. Recognition of the 67 kDa LR form of the laminin receptor by antibody S18 in the leucocyte fraction of the blood of cattle which are suffering from BSE. + cattle suffering from BSE; - healthy cattle.

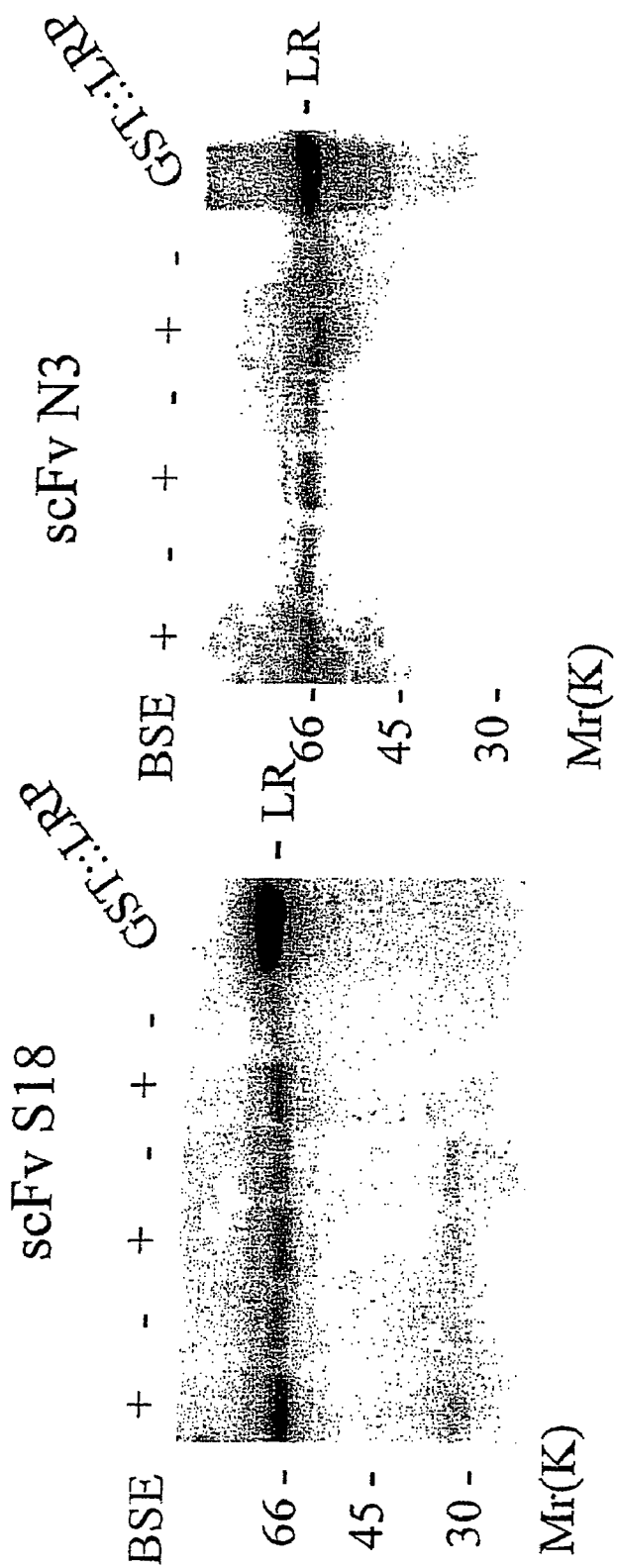
Fig. 15. Recognition of the 67 kDa LR form of the laminin receptor by antibodies S18 and N3 in the cerebraspinal fluid of cattle which are suffering from BSE and healthy cattle. + cattle suffering from BSE; - healthy cattle.

Fig. 16. scFvs S18 and N3 prevent the binding and internalization of exogenously tagged PrPc.

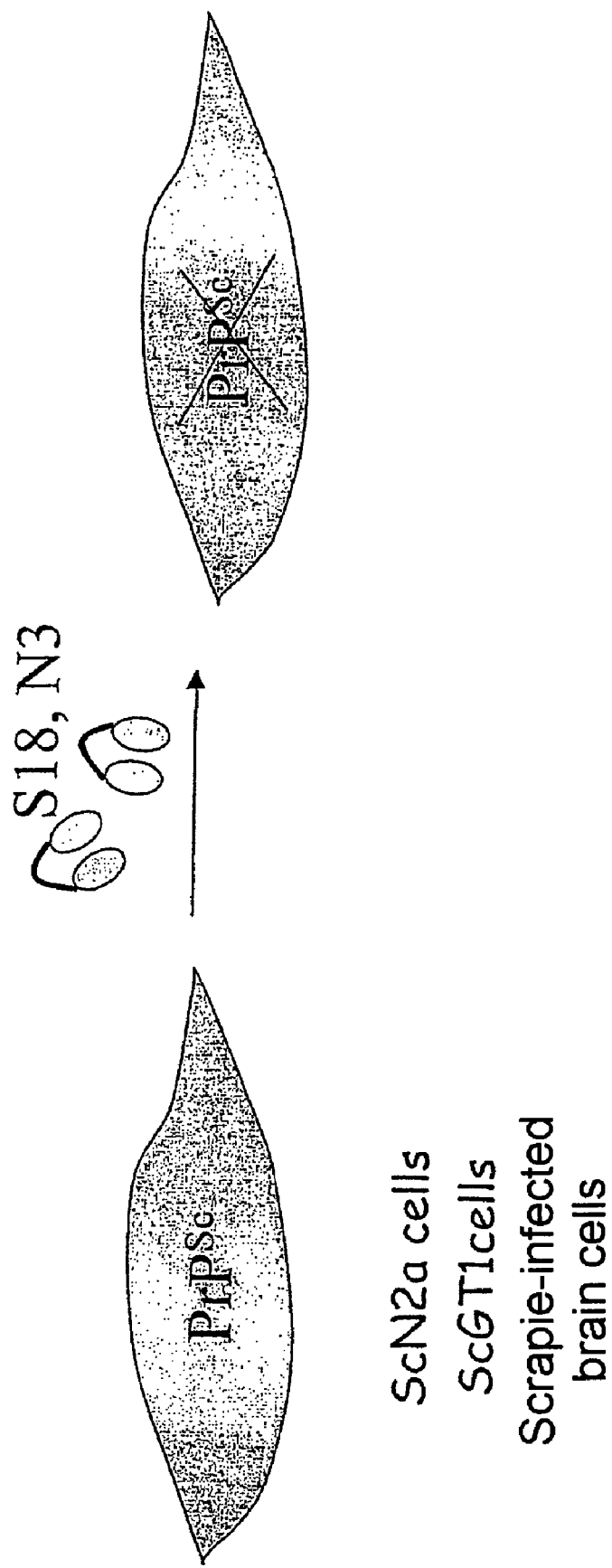
Fig. 17. scFvs S18 and N3 can cure PrP$^{Sc}$-proliferating cells of PrP$^{Sc}$.

Fig. 18. Preventive effect of scFvs S18 and N3 on scrapie-infectable cells.

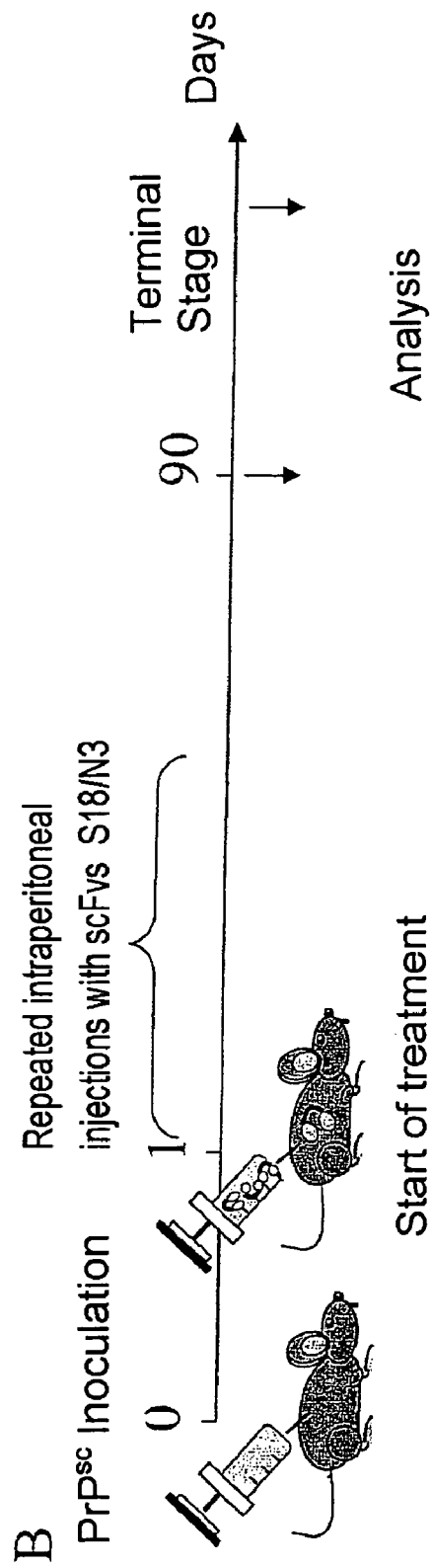
Fig. 19. In vivo effect of the scFv antibodies S18 and N3 in mice after inoculation with PrP^sc. Analysis of the dead time, the PrP^sc accumulation (brain + spleen), performance of psychomotor tests.

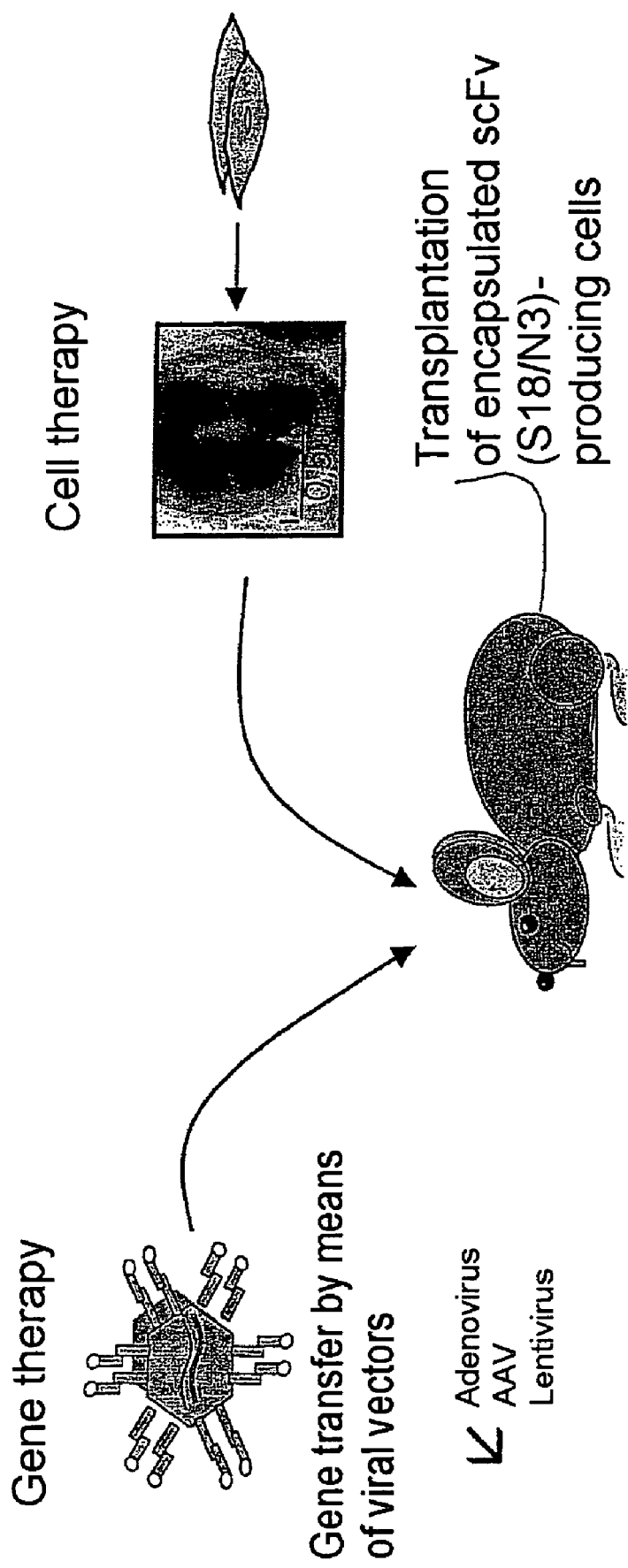
Fig. 20. Gene therapy and cell therapy for the treatment of TSEs in mice.

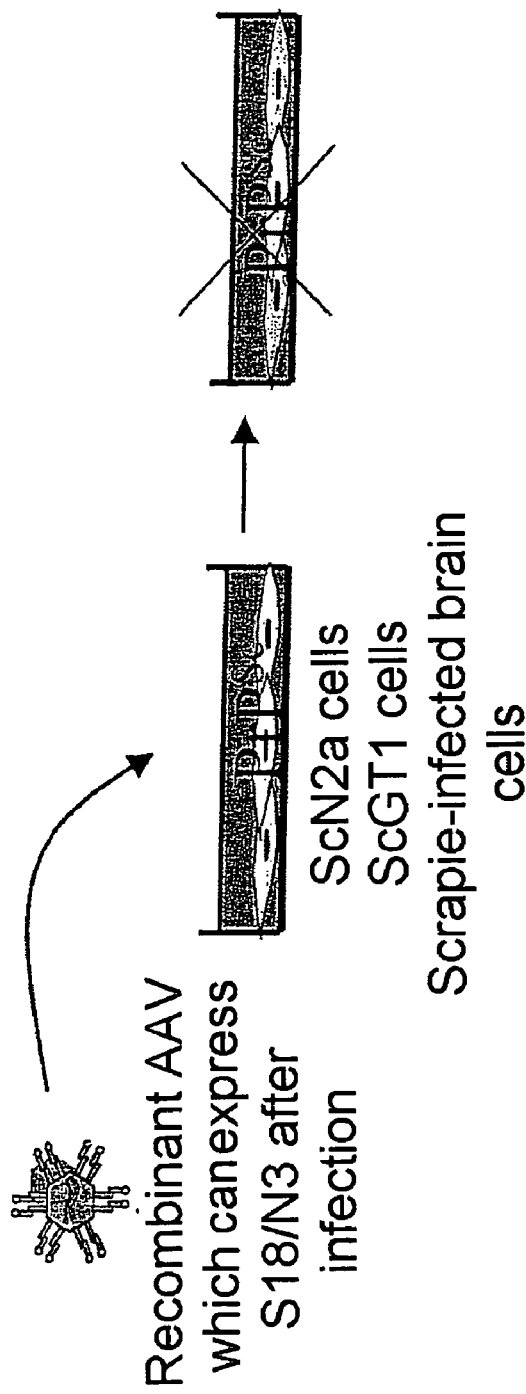
Fig. 21. Gene therapy with the aid of rec. AAVs which express scFvs S18 and N3. Rec. AAV cure scrapie-infected cells of scrapie after infection.

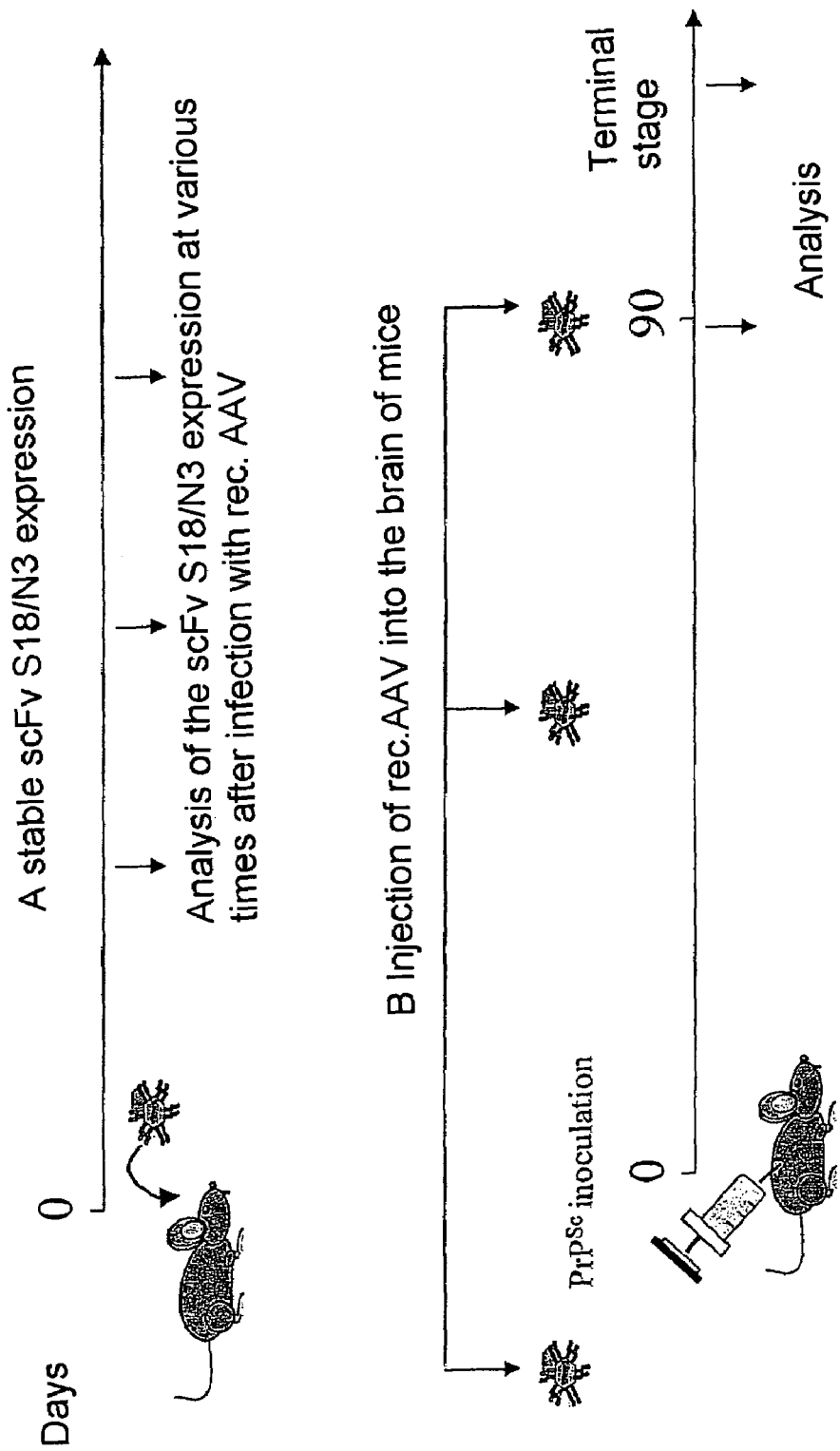
Fig. 22. Gene therapy with the aid of rec. AAVs which express scFvs S18 and N3. (A) Stable expression of scFvs S18 and N3 in the brain of mice. (B) Injection of rec. AAV which express S18/N3 at various times before and after a PrP$^{Sc}$ inoculation.

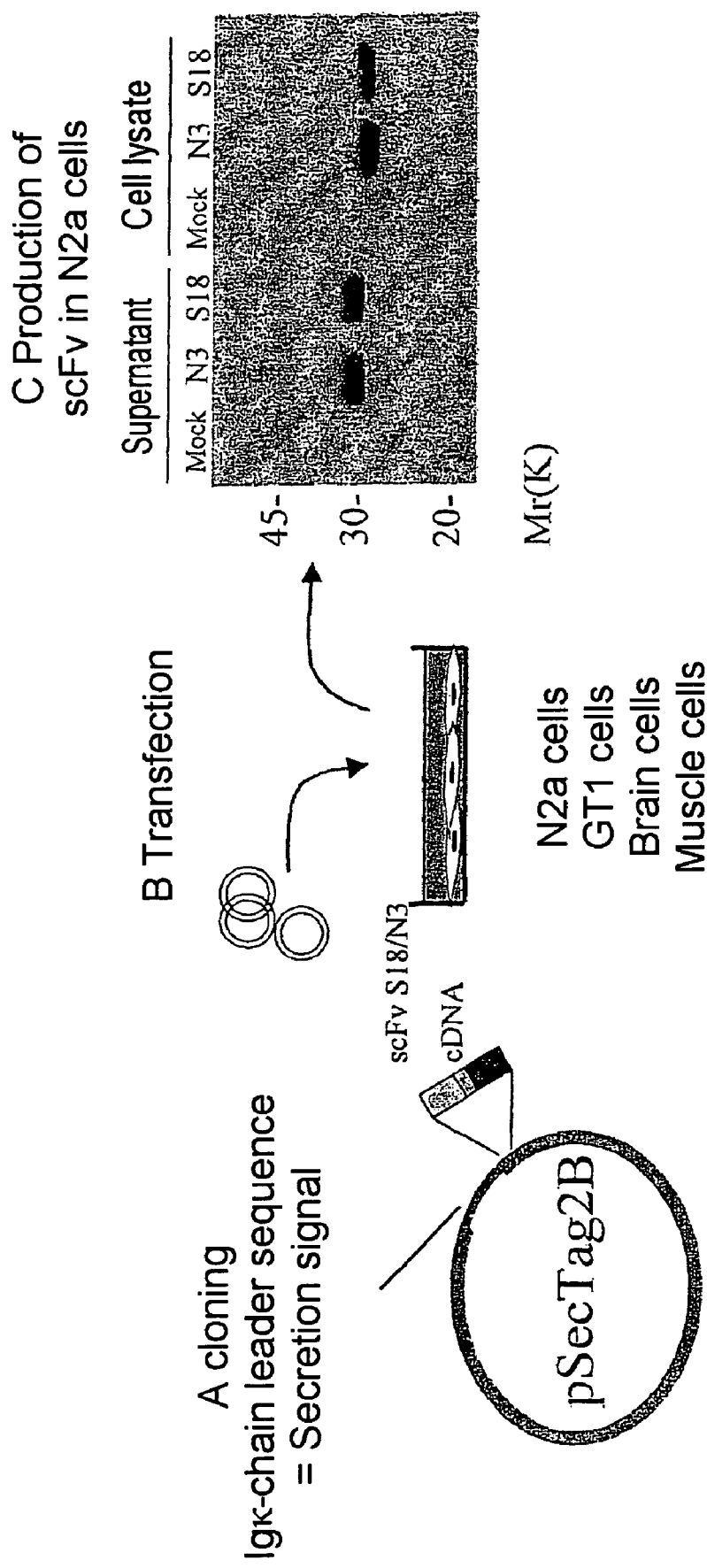
Fig. 23. Cell therapy for the treatment of TSEs in mice. (A) Cloning of scFv S18/N3 cDNA in pSecTag2. (B) Transfection in mammalian cells. (C) Secretion of the scFvs S18 and N3 in the medium of N2a cells.

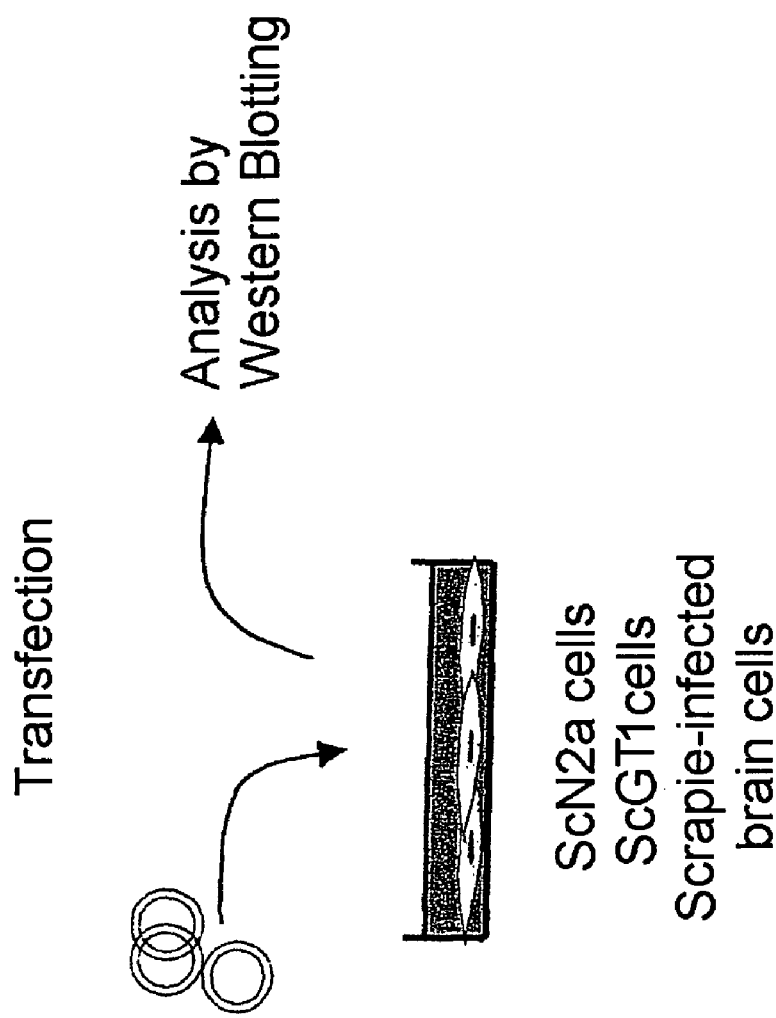
Fig. 24. Cell therapy for the treatment of TSEs in mice. The secretion of scFv S18/N3 from ScN2a/ScGT1 cells cures ScN2a/ScGT1 cells of scr

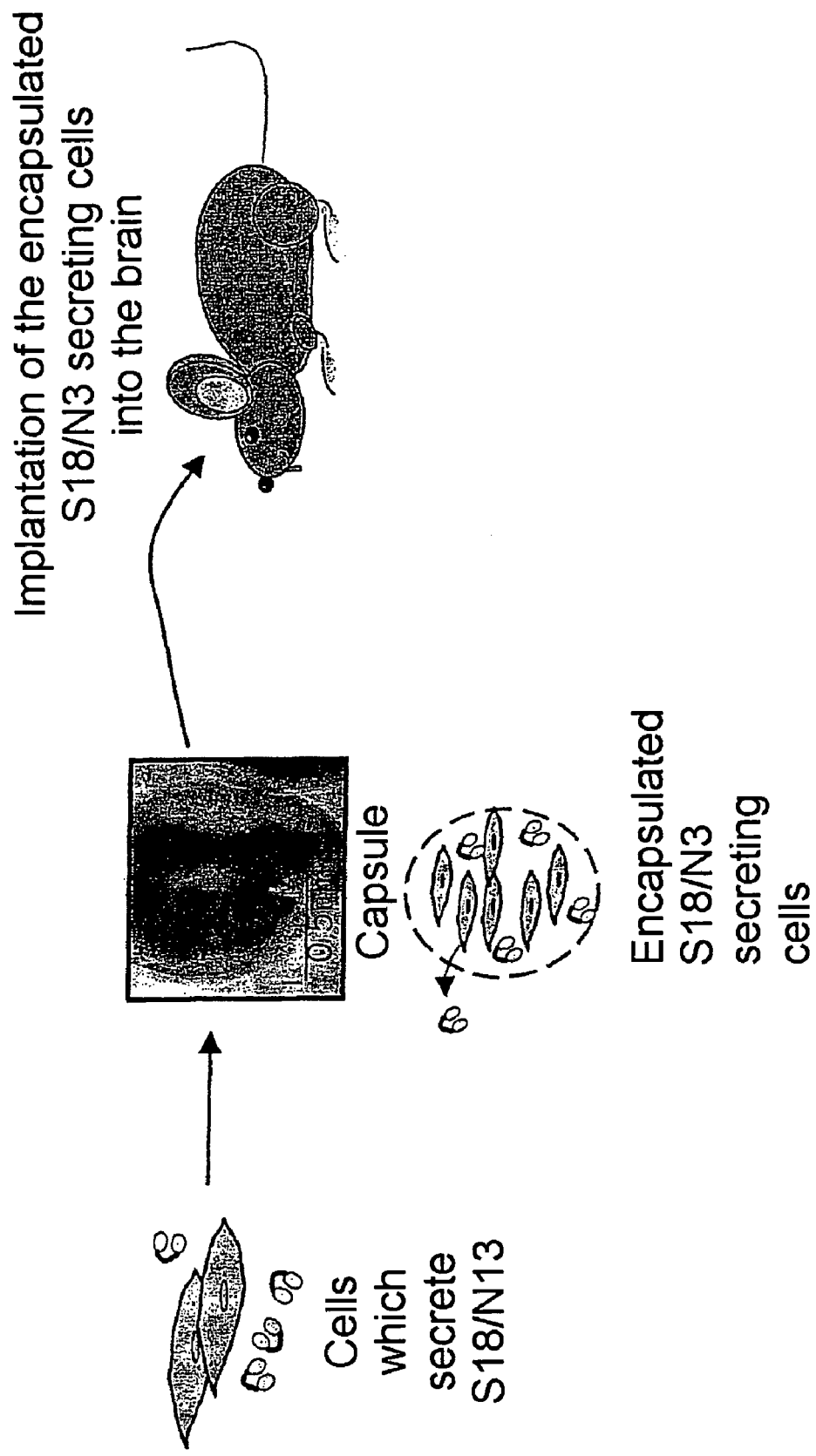
Fig. 25. Cell therapy with the aid of encapsulated cells (i.e. neuronal cells (PC12, N2a, GT1), muscle cells, BHK, NHI3T3, which secrete scFv S18/N3.

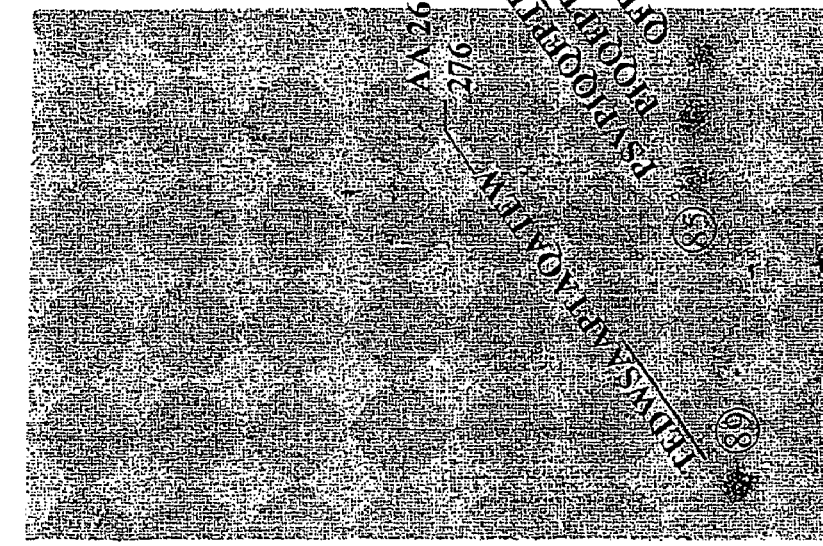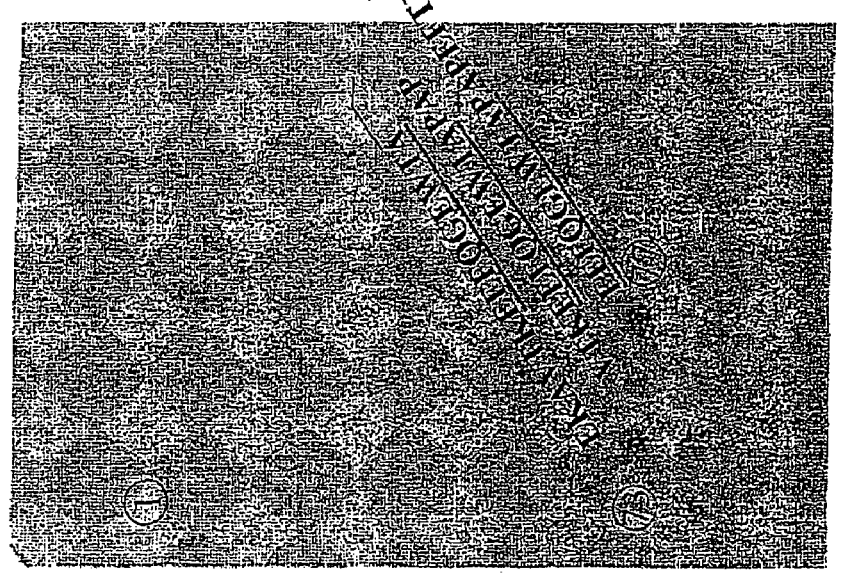
Fig. 26. Epitope mapping of the scFv antibodies S18 and N3.

Fig. 27. Schematic representation of the epitope mapping of the scFv antibodies S18 and N3. The epitope aa261-266 is shown, which binds to N3, and the epitope aa225-234), which binds to S18.

SEQUENCE LISTING

```
<160> NUMBER OF SEQ ID NOS: 4

<210> SEQ ID NO 1
<211> LENGTH: 816
<212> TYPE: DNA
<213> ORGANISM: artificial sequence
<220> FEATURE:
<223> OTHER INFORMATION: DNA codes for single-chain antibody scFv S18.
      It is contained in the plasmid pEX/HAM/LRP-S18. This plasmid was
      deposited in the DSMZ, Mascheroder Weg 1b, D-38124 under the
      accession number xxxx. After transformation of the plasmid in
      E.coli XL1-Blue, the production of the scFv antibody S18 is
      possible.

<400> SEQUENCE: 1
```

```
caggtgcagc tgcaggagtc tgggggaggc ttggtacagc ctgggggtc cctgagactc      60 tcctgtgcag cctctggatt catgtttagc aggtatgcca tgagctgggt ccgccaggct    120
ccagggaagg ggccagagtg ggtctcaggt attagtggta gtggtggtag tacatactac    180
gcagactccg tgaagggccg gttcaccgtc tccagagaca attccaagaa cacgctgtat    240
ctgcaaatga acagcctgag agccgaggac acggccgtat attactgtgc gagacatccg    300 ggttttttggc attttgacta ctggggccag gaactctgg tcaccgtctc ctcagggagt    360
gcatccgccc caaagcttga agaaggtgaa ttttcagaag cacgcgtatc tgaactgact    420
caggaccctg ctgtgtctgt ggccttggga cagacagtca ggatcacatg ccaaggagac    480
agcctcagaa actttatgc aagctggtac agcagaagc caggacaggc ccctactctt    540
gtcatctatg gtttaagtaa aaggccctca gggatcccag accgattctc tgcctccagc    600
tcaggaaaca cagcttcctt gaccatcact ggggctcagg cggaagatga ggctgactat    660
tactgtaact cccgggacag aagtggtaat catgtaaatg tgctattcgg cggagggacc    720
aagctgaccg tcctacgtca gcccaaggct gccccctcgg tcactctgtt cccgccctct    780
tctgcggccg ctggatccca tcaccatcac catcac                              816
```

<210> SEQ ID NO 2
<211> LENGTH: 272
<212> TYPE: PRT
<213> ORGANISM: artificial sequence
<220> FEATURE:
<223> OTHER INFORMATION: This protein corresponds to the single-chain
      antibody S18. It can be synthesized in E.coli XL1-Blue after
      transformation of the plasmid pEX/HAM/LRP-S18.

<400> SEQUENCE: 2

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Ala Met Ser Trp Val Arg Gln Ala Pro Gly Lys Gly Pro Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Gly Phe Trp His Phe Asp Tyr Trp Gly Gln Gly Thr
            100                 105                 110

Leu Val Thr Val Ser Ser Gly Ser Ala Ser Ala Pro Lys Leu Glu Glu
        115                 120                 125

Gly Glu Phe Ser Glu Ala Arg Val Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Asn Phe Tyr Ala Ser Trp Tyr Gln Gln Lys Pro Gly Gln
                165                 170                 175

Ala Pro Thr Leu Val Ile Tyr Gly Leu Ser Lys Arg Pro Ser Gly Ile
            180                 185                 190

Pro Asp Arg Phe Ser Ala Ser Ser Gly Asn Thr Ala Ser Leu Thr
        195                 200                 205
```

Ile Thr Gly Ala Gln Ala Glu Asp Glu Ala Asp Tyr Tyr Cys Asn Ser
        210                 215                 220

Arg Asp Arg Ser Gly Asn His Val Asn Val Leu Phe Gly Gly Gly Thr
225                 230                 235                 240

Lys Leu Thr Val Leu Arg Gln Pro Lys Ala Ala Pro Ser Val Thr Leu
                245                 250                 255

Phe Pro Pro Ser Ser Ala Ala Ala Gly Ser His His His His His His
            260                 265                 270

<210> SEQ ID NO 3
<211> LENGTH: 834
<212> TYPE: DNA
<213> ORGANISM: artificial sequence
<220> FEATURE:
<223> OTHER INFORMATION: DNA codes for single-chain antibody scFv N3.
      The DNA is contained in the plasmid pEX/HAM/LRP-N3. This plasmid
      was deposited in the DSMZ, Mascheroder Weg 1b, D-38124 under the
      accession number xxxx. After transformation of the plasmid in
      E.coli XL1-Blue, the production of the scFv antibody N3 is
      possible.

<400> SEQUENCE: 3
gaagtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg ggtggcagtt atatggtatg atggaagtaa taatactat     180 gcagactccg tgaagggccg attcaccatc tccagagaca attccaagaa cacgctgtat     240
ctgcaaatga acagcctgag agccgaggac acggctgtgt attactgtgc gactataccg     300
cgctcgtctt tctactacgg tatggacgtc tggggccaag gaccacggt caccgtctcc     360 tcagggagtg catccgcccc aacccttaag cttgaagaag gtgaattttc agaagcacgc     420
gtacagcctg tgctgactca gccacccta gcgtctggga ccccagggca gagggtcacc     480
atctcttgtt ctggaagcag atccaacatc ggaagtaata ctgtaaactg gtaccagcag     540
ctcccaggaa cggcccccaa actcctcatc tatggtaata tcagcggcc ctcaggggtc     600 cctgagcgat tctctggctc caagtctggc acctcagcct ccctggccat cagtgggctc     660
cagtcagagg atgaggctga ttattactgt gcagcgtggg atgacagcct gactggtgtg     720
cttttcggcg gagggaccaa gctgaccgtc ctaggtcagc ccaaggctgc ccctcggtc     780 actctgttcc cgccctcttc tgcggccgct ggatcccatc accatcacca tcac            834

<210> SEQ ID NO 4
<211> LENGTH: 278
<212> TYPE: PRT
<213> ORGANISM: artificial sequence
<220> FEATURE:
<223> OTHER INFORMATION: This protein corresponds to the single-chain
      antibody N3. It can be synthesized in E.coli XL1-Blue after
      transformation of the plasmid pEX/HAM/LRP-N3.

<400> SEQUENCE: 4

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

-continued

```
Lys Gly Arg Phe Thr Ile Ser Arg Asp Asn Ser Lys Asn Thr Leu Tyr
 65              70              75              80

Leu Gln Met Asn Ser Leu Arg Ala Glu Asp Thr Ala Val Tyr Tyr Cys
             85              90              95

Ala Thr Ile Pro Arg Ser Ser Phe Tyr Tyr Gly Met Asp Val Trp Gly
            100             105             110

Gln Gly Thr Thr Val Thr Val Ser Ser Gly Ser Ala Ser Ala Pro Thr
            115             120             125

Leu Lys Leu Glu Glu Gly Glu Phe Ser Glu Ala Arg Val Gln Pro Val
        130             135             140

Leu Thr Gln Pro Pro Ser Ala Ser Gly Thr Pro Gly Gln Arg Val Thr
145             150             155             160

Ile Ser Cys Ser Gly Ser Arg Ser Asn Ile Gly Ser Asn Thr Val Asn
                165             170             175

Trp Tyr Gln Gln Leu Pro Gly Thr Ala Pro Lys Leu Leu Ile Tyr Gly
            180             185             190

Asn Asn Gln Arg Pro Ser Gly Val Pro Glu Arg Phe Ser Gly Ser Lys
            195             200             205

Ser Gly Thr Ser Ala Ser Leu Ala Ile Ser Gly Leu Gln Ser Glu Asp
        210             215             220

Glu Ala Asp Tyr Tyr Cys Ala Ala Trp Asp Asp Ser Leu Thr Gly Val
225             230             235             240

Leu Phe Gly Gly Gly Thr Lys Leu Thr Val Leu Gly Gln Pro Lys Ala
            245             250             255

Ala Pro Ser Val Thr Leu Phe Pro Pro Ser Ser Ala Ala Ala Gly Ser
            260             265             270

His His His His His His
            275
```

SINGLE-CHAIN ANTIBODY ACTING AGAINST 37 KDA/67 KDA LAMININ RECEPTOR AS TOOLS FOR THE DIAGNOSIS AND THERAPY OF PRION DISEASES AND CANCER, PRODUCTION AND USE THEREOF

The present invention lies in the field of antibodies which are directed against the cell surface receptor of prion proteins, the 37 kDa/67 kDa laminin receptor. In particular, the present invention relates to single-chain antibodies which specifically recognize both the 37 kDa precursor form of the laminin receptor (37 kDa LRP) and the 67 kDa high-affinity form of the laminin receptor (67 kDa LR).

Prion proteins, which are involved in the occurrence of very different forms of transferable spongiform encephalopathies (TSEs), such as scrapie in sheep, mice and hamsters, transferable spongiform encephalopathy of cattle (BSE), transferable spongiform encephalopathy in mink (TME), kuru, Gerstmann-Sträußler-Scheinker syndrome (GSS), Creutzfeldt-Jakob disease (CJD) and fatal familial insomnia (FFI) in man, consist mainly, even if not entirely, of $PrP^{Sc}$, an anomalous isoform of the ubiquitous cellular prion protein $PrP^c$ (see, for example, Aguzzi and Weissmann, 1998; Lasmézas and Weiss, 2000; Prusiner et al., 1998).

It is known from WO 98/53838 and from Rieger et al. (Rieger et al., 1997) that the $PrP^c$ binds specifically to the cell surface receptor of prion proteins, the 37 kDa LRP/67 kDa LR. It is known from WO 98/53838 and from EP-A-1 127 894 and from Rieger et al. (Rieger et al., 1997) that the laminin receptor level in tissues of animals infected with scrapie, such as hamsters and mice, is increased.

Gauczynski et al., 2001b show that the 37 kDa LRP/67 kDa LR functions as a receptor for $PrP^c$. Binding sites on both molecules have been mapped (Hundt et al., 2001) and heparan sulfate proteoglycans (HSPGs) identified as cofactors or coreceptors for $PrP^c$ (Hundt et al., 2001).

The 37 kDa laminin receptor precursor (37 kDa LRP, p40, LBP) is the precursor protein of the 67 kDa high affinity laminin receptor (67 kDa LR) (Rao et al., 1989; Yow et al., 1988).

The 67 kDa form was initially isolated from tumor cells (Lesot et al., 1983; Malinoff and Wicha, 1983; Rao et al., 1983), where the protein has a high affinity to laminin.

The 37 kDa/67 kDa laminin receptor is furthermore overexpressed in tumor tissues (Lesot et al., 1983; Malinoff and Wicha 1983; Rao et al., 1983).

Laminin is a glycoprotein of the extracellular matrix, where it is involved in the adhesion, motion, differentiation and growth of cells (Beck et al., 1990). Both forms of the laminin receptor exist together in mammalian cells, which it was possible to show by immunological studies of membrane fractions (Gauczynski et al., 2001b).

The 37 kDa form also occurs in the cytosol, where it is associated with ribosomes and can take over tasks in protein translation (Auth and Brawermann, 1992; Sato et al., 1999). The existence of this protein in the nucleus was also discussed, where it should also be involved in the maintenance of structures (Kinoshita et al., 1998; Sato et al., 1996).

LRP/LR is a multifunctional protein which, starting from the gene product p40, can form two different forms, occurs in various cell compartments and exerts different functions there. The amino acid sequence of the 37 kDa/67 kDa laminin receptor is highly conserved, with a high homology in mammals (Rao et al., 1989). By means of an evolution analysis of the amino acid sequence, it was possible to show that the palindromic sequence LMWWML is responsible for the ability to bind laminin. This sequence lies in the PrP-binding region of the 37 kDa LRP (Ardini et al., 1998; Hundt et al., 2001; Rieger et al., 1997).

It appears that the ribosomal protein p40, which initially did not possess the ability to bind laminin (Auth and Brawerman, 1992), evolved in the course of evolution by amino acid exchange and introduction of post-translational changes to a laminin-binding cell surface protein which can also bind elastin (Hinek et al., 1988; Salas et al., 1992) and carbohydrate chains (see, for example, Ardini et al., 1998; Mecham, 1991; Rieger et al., 1999).

The laminin receptor family is highly conserved in many eukaryotic cells (Keppel and Schaller, 1991; Wewer et al., 1986) and can also be found in *Archaea* (Ouzonis et al., 1995).

The 37 kDa LRP functions as a receptor for the Venezuelan equine encephalitis virus on mosquito cells (Ludwig et al., 1996), while the 67 kDa form can obviously be used as a receptor for the Sindbis virus (Wang et al., 1992).

With respect to the processes underlying the conversion of the 37 kDa form to the 67 kDa protein, it is known that both proteins consist of the 37 kDa component, a number of proposals having been made to explain the greater mass of the mature protein. Homodimerization of the 37 kDa protein and also binding to another component have been discussed (Castronovo et al., 1991; Landowski et al., 1995). Other studies, however, propose a heterodimer stabilized by fatty acids (Buto et al., 1998). It has recently been shown that the 67 kDa laminin receptor also occurs on activated human T lymphocytes and has a strong affinity there, together with integrins, to laminin (Canfield and Khakoo, 1999).

It is to be emphasized, however, that currently the 37 kDa/67 kDa polymorphism is not conclusively explained.

The 37 kDa/67 kDa laminin receptor is represented by a number of genes in the genome of mammals. In man, there are 26, in the mouse 6, copies (Fernandez et al., 1991; Jackers et al., 1996b). The gene consists of seven exons and six introns, most gene copies probably being pseudogenes (Jackers et al., 1996a). In the mouse, there are hints that at least two of the six genes are active and situated on chromosome 9 (Douville and Carbonetto, 1992; Fernandez et al., 1991). With the aid of TRIBE-MCL, an algorithm for the detection of protein families (Enright et al., 2002), five LRP genes were identified when using the program for the screening of the relevant mouse genome sequence data bank (www.ensembl.org). Interestingly, it was recently shown that on chromosome 9 are possibly situated gene loci which influence the incubation time of prion diseases in mice (Stephenson et al., 2000).

The gene which codes for the 37 kDa LRP has been identified in many different species, such as *Saccharomyces cerivisiae* (Davis et al., 1992), *Arabidopsis thaliana* (Garcia-Hernandez et al., 1994), *Drosophila melanogaster* (Melnick et al., 1993), the sea urchin *Urechis caupo* (Rosenthal and Wordeman, 1995), *Chlorohydra veridissima* (Keppel and Schaller, 1991), *Candida albicans* (Lopez-Ribot et al., 1994) and the Archaebacterium *Haloarcula marismortui* (Ouzonis et al., 1995) and the mammals (see, for example, Gauczynski et al., 2001a; Leucht and Weiss, 2002; Rieger et al., 1999).

It is known from WO 98/53838 and from a later publication (Leucht et al., 2003) that the polyclonal LRP antibody W3 prevents $PrP^{Sc}$ replication in cultured neuronal cells. Generally, this shows that antibodies against 37 kDa LRP/67 kDa LR can completely suppress prion replication at least in cell culture. Interestingly, the cells also then remained free of $PrP^{Sc}$ (Leucht et al., 2003) if, after further culturing for a further two weeks, no LRP/LR antibody was added. Generally, this shows that LRP/LR antibodies are able to completely cure prion-infected cell cultures of a prion infection.

Furthermore, it is known from EP-A-1 127 894 that LRP/LR antibodies can be employed diagnostically for the recognition of prion diseases, since the LRP/LR level is increased in tissues of rodents infected with scrapie.

Polyclonal antibodies against LRP/LR, which are described in WO 98/53838 and EP-A-1 127 894, possess the disadvantage, however, that they can only be selected with difficulty, are very large and exhibit high immunogenicity. In contrast to single-chain antibodies, which can be synthesized in large amounts in E. coli, these antibodies are only available to a restricted extent.

It was consequently the object of the present invention to make available novel monoclonal antibodies which specifically recognize LRP/LR, which are easy to select, are distinguished by a small size and have low immunogenicity.

The subject of a first aspect of the present invention is a single-chain antibody molecule, which is directed specifically against LRP/LR and which comprises the amino acid sequence SEQ ID No. 2, and homologs or fragments thereof, and homologs of the fragments.

The subject of a further aspect of the present invention is a single-chain antibody molecule, which is directed specifically against LRP/LR and which comprises the amino acid sequence SEQ ID No. 4, and homologs or fragments thereof, and homologs of the fragments.

A homolog of the antibody molecule which comprises the amino acid sequence SEQ ID No. 2 or 4 is customarily homologous to at least 70%, preferably to 80 or 90% and in particular to 95%, to the antibody molecule comprising the amino acid sequence SEQ ID No. 2 or 4 over a region of at least 60, 80 or 100 or more adjacent amino acids.

In general, a fragment of the antibody molecule according to the invention which comprises the amino acid sequence SEQ ID No. 2 or 4, or a homolog thereof, has an amino acid length of at least 30, 40, 50 or 60 amino acids.

The subject of a further aspect of the present invention is a cDNA which codes for the antibody molecule having the designation S18, which is directed against LRP/LR and which comprises the nucleotide sequence SEQ ID No. 1, and a fragment cDNA which selectively hybridizes to the cDNA.

The subject of a further aspect of the present invention is a cDNA which codes for the antibody molecule having the designation N3, which is directed against LRP/LR and which comprises the nucleotide sequence SEQ ID No. 3, and a fragment cDNA which selectively hybridizes to the cDNA.

A cDNA having the ability for selective hybridization to the cDNA which comprises the nucleotide sequence SEQ ID No. 1 or 3 is customarily homologous to at least 70%, preferably to 80 or 90% and in particular to 95%, to the cDNA comprising the nucleotide sequence SEQ ID No. 1 or 3 over a region of at least 60, 80 or 100 or more adjacent nucleotides.

The subject of a further aspect of the present invention is a replication or expression vector which carries the cDNA according to the invention. The vectors can, for example, be plasmid, virus or phage vectors which comprise a replication origin and optionally a promoter for the expression of the cDNA and optionally a regulator of the promoter. The vector can contain one or more selectable marker genes, for example the ampicillin resistance gene. The vector can be used in vitro, for example for the production of RNA corresponding to the cDNA, or for the transfection of a host cell. Suitable vectors are, for example, viral vectors (lentiviruses, adenoviruses, adeno-associated viruses (AAV)).

The subject of a further aspect of the present invention are host cells which are transformed with the vectors for the replication and expression of the cDNA according to the invention, including the cDNA which comprises the nucleotide sequence SEQ ID No. 1 or 3 or the open reading frame thereof. The cells are chosen such that they are compatible with the vector. Examples of these are bacteria, yeast, insect cells or mammalian cells, in particular E. coli cells or mammalian cells.

The subject of a further aspect of the present invention is a process for the production of an antibody molecule, which comprises culturing host cells according to the present invention under conditions effective for the expression of an antibody molecule according to the invention.

The subject of a further aspect of the present invention are pharmaceutical compositions which comprise an antibody molecule according to the invention in combination with a pharmaceutically acceptable diluent and/or vehicle.

In a further preferred embodiment, the abovementioned pharmaceutical composition is suitable for the treatment of prion diseases.

The subject of a further aspect of the present invention are diagnostic compositions which comprise an antibody molecule according to the invention in combination with an acceptable diluent and/or vehicle.

The antibody molecule described above also comprises those in which a part of their amino acid sequence is missing (i.e. an antibody molecule which only comprises the essential sequence for the display of the biological activity of the amino acid sequence indicated in SEQ ID No. 2 or 4), those in which a part of their amino acid sequence is replaced by other amino acids (i.e. in which an amino acid is replaced by an amino acid of similar property) and those in which other amino acids are added to or inserted in a part of their amino acid sequence.

FIG. 1 shows the schematic representation of a single chain (single-chain antibody) scFv in comparison with the antibody having the full length, consisting of a Fab and Fc part. The scFv consists of a part of the heavy chain ($V_H$) and a part of the light chain ($V_L$). Both parts originate from the Fab part of an antibody which is responsible for antigen recognition. $V_H$ and $V_L$ are connected by a linker (YOL).

FIG. 2 shows schematically the naive scFv bank which was used for the screening of the scFv antibody directed against GST::LRP. The naive bank contains approximately $2 \times 10^9$ clones and was generated by the combination of the coding regions for the heavy ($V_H$) and light ($V_L$) chains after PCR amplification of the respective cDNA from spleen or PBLs (peripheral blood lymphocytes).

FIG. 3 shows schematically the synthetic scFv bank consisting of selected frameworks having good folding properties and high expression rates and comprising randomized sequences in their CDR3 regions. The bank contains approximately $1 \times 10^9$ clones.

FIG. 4 shows schematically the screening process by means of phage display. In this process, the naive or synthetic scFv banks shown in FIG. 2 and FIG. 3 are employed. The antigen GST::LRP described in WO 98/53838 was immobilized on polystyrene tubes. Only phages which present scFv which bind GST::LRP are selected. Nonspecifically bound phages are washed off. Amplification of these phages follows, these being enriched by means of three successive selection rounds.

FIG. 5 shows an ELISA of periplasmatic crude extracts of clones obtained after three selection rounds from the naive scFv bank. The extracts were tested on recombinant GST::LRP fusion protein. The result is shown in FIG. 7 in tabular form. K=only secondary antibody.

FIG. 6 shows an ELISA of periplasmatic crude extracts of clones obtained after three selection rounds from the synthetic scFv bank. The extracts were tested on recombinant GST::LRP fusion protein. The result is shown in FIG. 7 in tabular form. K=only secondary antibody.

FIG. 7 compiles the result of the ELISAs from FIGS. 5 and 6 schematically. 32 of 48 clones (66%) in the case of the naive bank (FIG. 5) and 25 of 47 clones (53%) from the synthetic bank showed positive signals. Furthermore, retesting of 13 clones from the naive and 6 clones from the synthetic banks on GST (without a fusion partner) was carried out. GST was not recognized, which allows it to be concluded that the scFvs only recognize the LRP part of the fusion protein. A restriction analysis of the cDNAs of the 13 clones from the naive bank with BstNI showed that 10 clones were identical (10/13). A further clone was identified twice (2/13). One clone (N37) showed an individual restriction pattern.

FIG. 8 shows the detection of recombinant GST::LRP by individual clones selected from the synthetic (S) and naive (N) scFv banks. Selected clones which were identified by means of ELISA (FIGS. 5 and 6) were tested in the Western Blot. In each track, a mixture of rec. GST and GST::LRP expressed in the Baculovirus system was separated on a 12% strength SDS-PA gel. The proteins were blotted on a nitrocellulose membrane. The individual tracks of the blots were cut out and the individual strips were incubated with periplasmatic extracts of the selected individual scFvs from the naive and synthetic banks or respective controls. The polyclonal anti-LRP antiserum W3 known from WO 98/53838 was detected using a polyclonal goat anti-rabbit (hare) HRP conjugate (Dianova). The scFvs were detected using a monoclonal mouse anti-penta-histidine antibody (Qiagen) followed by a goat anti-mouse HRP conjugate (Dianova). Anti-rabbit-HRP: only goat anti-hare conjugate. Anti-His: monoclonal mouse anti-histidine antibody with a further goat anti-mouse HRP conjugate. Anti-mouse HRP: only goat anti-mouse HRP conjugate. MluC5: monoclonal anti-LRP antibody, which does not function in the Western Blot analysis.

The scFvs N3, and S18 and S23 produced strong signals. None of the scFv antibodies recognized rec. GST, which shows that all scFvs recognize the LRP part.

FIG. 9 shows the detection of LRP/LR on the surface and intracellularly of N2a cells.

Surface: The cells were incubated with 100 µg/ml of anti-LRP antiserum W3 (WO 98/53838), then with the FITC-conjugated goat anti-hare IgG.

scFv anti-LR/LRP N3 and S18 were employed at in each case 18 µg/ml and detected using monoclonal anti-His antibody (1:20; Dia900) followed by FITC-conjugated goat anti-mouse IgG.

Intracellular: The cells were fixed with 3% paraformaldehyde, and incubated with 50 mM $NH_4Cl$/20 mM glycine before staining with the antibodies described above with the following modification: all washing and incubation steps were carried out at room temperature in a 0.1% saponin-containing buffer. The scFv antibodies were in each case employed at concentrations to 9 µg/ml.

FIG. 10 shows the detection of LRP/LR on the surface and intracellularly of Jurkat cells (human, peripheral blood leukemia T cells). The antibodies, secondary and tertiary antibodies used correspond to those described in the legend of FIG. 9. The method used corresponds to that described in FIG. 9 apart from the fact that Jurkat cells were used.

FIG. 11 shows the detection of recombinant LRP::FLAG or endogenous LRP/LR in baby hamster kidney cells (BHK) transfected with SFV1-huLRP-FLAG or SFV1-moLRP::FLAG. BHK cells were either not transfected (n.t.) or transfected in the manner known to the person skilled in the art in the specialty with the rec. Semliki forest virus (SFV) RNAs SFV1-huLRP-FLAG or SFV1-mol.RP::FLAG. The method of preparation of rec. SFV RNA, the transfection and the analysis by Western Blotting or immunofluorescence (FIG. 12) or FACS (FIG. 13) have already been described (Gauczynski et al., 2002; Gauczynski et al., 2001b). 24 h post-transfection, total cell extracts were analyzed by Western Blotting. The total cell extracts were separated on a 12% strength PA gel, then the proteins were blotted on PVDF membrane. As primary antibodies, the scFvs S18 (C) and N3 (A) (dilution in each case 1:1000) were employed, coupled as a secondary antibody mouse anti-c-myc (1:1000) as a tertiary antibody anti-mouse HRP (horseradish peroxidase). The control used was the anti-LRP antibody mLRP43512 (A), and an anti-mouse IgG-HRP-coupled secondary antibody. As a loading control, the β-actin level was determined. To this end, an anti-β-actin antibody (Chemicon) was employed. Detection was carried out by chemiluminescence (Western Lightning, NEN). The svFvS18 and N3 specifically recognize the rec. LRP::FLAG. S18 and N3 recognize endogenous LRP (B,C). N3 recognizes endogenous LR (67 kDa) (B).

FIG. 12. Immunofluorescence analysis of LRP/LR in BHK cells transfected with recombinant SFV RNA. BHK cells were not transfected, as described in FIG. 11, or transfected with the rec. SFV RNAs SFV-1-muLRP-FLAG and SFV-1-huLRP-FLAG. The scFv antibodies S18 and N3 and the W3 antibody known from WO 98/53838 were in each case employed 1:100. For S18 and N3, an Anti-c-myc-FITC-coupled secondary antibody in each case was employed 1:500. For W3, an anti-rabbit Cy2-coupled antibody (1:500) was employed. As a control, only the secondary antibody anti-c-myc FITC (1:500) was employed. The nucleus was stained with DAPI. This staining cannot be seen in the Fig. Cells were fixed using 4% paraformaldehyde. The cells were not permeabilized, which guarantees cell surface staining. The Fig. shows that the scFv S18 and N3 detect LRP::FLAG on the surface of the transfected cells. Both scFv S18 and N3 are also able to detect endogenous LRP (2nd and 3rd left picture from above).

FIG. 13 shows an FACS analysis of BHK cells which were not transfected or were transfected with the recombinant SFV RNAs SFV-1-huLRP-FLAG or SFV-1-muLRP-FLAG. ScFVS18 and N3 were employed in the conc. 18 µg/ml, the W3 antibody and the anti-galectin-3 antibody at 100 µg/ml. Secondary antibody: anti-c-myc FITC-coupled for S18 and N3, anti-rabbit Cy2 for W3 and anti-mouse Cy2-coupled for anti-gal3 antibody (dilution of the secondary antibody 1:500). Cells were not permeabilized, which guarantees cell surface staining. The figure shows that scFv S18 and N3 can detect LRP::FLAG on the cell surface of living cells.

FIG. 14 shows the detection of an increased LR level in the leucocyte fraction of the blood of cattle which are suffering from BSE in the Western Blot by the scFv S118. The blood samples (500 µl) of cattle suffering from BSE and healthy cattle were mixed 1:1 with 1×SSC, and centrifugation at 4000 rpm/10 min. Removal of the supernatant, resuspend pellet in 1×SSC, centrifuge again and remove the supernatant. Wash pellet until pellet is white. The white leucocyte pellet is resuspended in 100 µl of TBS. The leucocytes are analyzed on a 12.5% strength PA gel. As a control, GST::LRP from the Baculovirus expression system is applied. The proteins are blotted on a PVDF membrane and with the scFv antibody S18 (1:1000; approximately 2 µg/ml) and, as a control of the detection of the β-actin level, measured off with an anti-β-actin antibody (Chemicon). For scFv S18: secondary antibody, anti-c-myc (1:1000), tertiary antibody goat anti-mouse IgG-HRP-coupled (1:5000). GST::LRP was coupled via the W3 antibody, sec. antibody anti-rabbit IgG-HRP. The figure shows an increased LR level in the leucocyte fraction of cattle suffering from BSE.

FIG. 15 shows the detection of an increased LR level in the cerebrospinal fluid (CSF) of animals suffering from BSE in comparison with healthy control animals. Identical amounts of protein were applied. As a positive control, GST::LRP (rec. from Baculovirus system) was applied. Total cerebrospinal fluid was separated on a 12.5% strength PA gel and blotted on a PVDF membrane. scFv S18 and N3 in each case diluted 1:1000 (about 2 µg/ml each), secondary antibody mouse anti-c-myc (1:1000), tertiary antibody goat anti-mouse IgG-HRP-coupled. Detection via chemiluminescence. The figure shows an increased LR level detected by scFv S18 and N3 in the CSF of cattle suffering from BSE.

FIG. 16 shows schematically that scFv S18 and N3 can prevent the binding and internalization of exogenously tagged $PrP^c$. The Fig. shows a possible mechanism of action of svFv S18 and N3, namely the blocking of the uptake of the cellular form of the prion protein.

FIG. 17 shows schematically that scFv antibody S18 and N3 added to cells infected with scrapie can cure the cells of a scrapie infection (therapeutic mechanism of action).

FIG. 18 shows schematically a prophylactic mechanism of action of scFv S18 and N3. If both antibodies are added to non-infected cells, they prevent the cells from being infected with scrapie (prophylactic mechanism of action).

FIG. 19 shows schematically the therapeutic in vivo application of the scFv antibodies S18 and N3 in animals (Passive Antibody Transfer). (A) The antibodies are initially injected, preferably intraperitoneally, into healthy animals, preferably hamsters or mice, in order to detect possible specific and nonspecific (i.e. inflammatory response) side effects of the antibodies. (B) The scFv antibodies S18 and N3 are then begun with intraperitoneal administration at various times after a PrPSc inoculation—preferably one day after the $PrP^{Sc}$ inoculation. Furthermore, the antibodies are administered repeatedly according to the following protocol: An initial dose of in each case 200 μg of the S18 and N3 antibodies is injected intraperitoneally (i.p.), preferably into C57/BL6 mice, one day after intraperitoneal inoculation with a prion strain, preferably the BSE strain 6PB1. I.p. injections twice a week with 100 μg of the scFv S18/N3 follow for preferably a further eight weeks. Some of the animals are sacrificed 90 days p.i. and investigated biochemically for $PrP^{Sc}$ presence. The other animals are either investigated at the terminal stage of a TSE disease or, if no symptoms occurred, at the end of their lifetime.

FIG. 20 shows the gene therapy and cell therapy approach for the treatment of prion diseases with the aid of the scFv antibodies S18 and N3. The gene therapy approach uses viral vectors, preferably AAV, in order to transfer genes which code for S18 and N3 to animals or man. The cell therapy approach is carried out by transplantation of encapsulated cells which secrete the scFv antibodies S18 and N3. Both approaches are explained in greater detail in the following figures.

FIG. 21 shows the use of recombinant AAV viruses which can express scFv S18/N3 on cells infected with scrapie. The infection of neuronal cells infected with scrapie with recombinant S18/N3-expressing AAV viruses should cure these cells of scrapie.

FIG. 22 shows the gene therapy approach with recombinant AAV viruses which express S18/N3 in vivo in mammals (including man), preferably mice. (A) After injection of the recombinant AAV viruses directly into the brain of healthy animals, the expression of the scFV antibodies S18 and N3 is checked by Western Blot analysis of the brain fractions. (B) Mice are injected before, during or after a $PrP^{Sc}$ inoculation with recombinant S18/N3-expressing AAV viruses. A delay in the outbreak of a TSE disease of the mice is determined by psychomotor tests and histological and immunohistochemical analysis of the brain.

FIG. 23 shows the cloning and expression/secretion of scFv antibodies S18 and N3 from neuronal cells and schematically from muscle cells. (A) The cDNA which codes for S18 and N3 is cloned via the restriction sites HindIII/NotI into the secretion vector pSecTag2B. (B) Neuronal cells are transfected with rec. pSecTag2B, which encodes S18 and N3. (C) 24 hours post-transfection (p.t.), transfected cells show the expression and secretion of S18 and N3 by Western Blotting (1st antibody: anti-c-myc; 2nd antibody: anti-mouse IgG-HRP-conjugated. Detection via chemiluminescence). The figure shows that the scFv S18 and N3 can be secreted from N2a cells.

FIG. 24 shows the administration of S18/N3-secreting ScN2a cells. After transfection of scrapie-propagating cells, these should be cured of $PrP^{Sc}$.

FIG. 25 shows schematically cell therapy by scFv S18/N3-secreting cells, preferably muscle cells or neuronal cells, BHK cells or NIH3T3 cells, which are encapsulated and are transplanted into the brain of mammals including man. By means of the secretion of scFv S18/N3, the prion propagation in the brain of the organism should be stopped.

FIG. 26 shows the epitope mapping of the scFv S18/N3 antibody.

FIG. 27 shows a schematic representation of the epitope mapping of the scFv S18/N3 antibody.

LIST OF ABBREVIATIONS

Ab=antibody
AAV=adeno-associated virus
BHK=baby hamster kidney cells
BSE=bovine spongiform encephalopathy
BSE+=cow which is suffering from BSE
BSE−=cow which is healthy
CDR1/2/3=complementary determining region 1/2/3
(s/f/nv) CJD=(sporadic/familial/new variant) Creutzfeldt-Jakob disease
c-myc=epitope from the corresponding oncogene
CMV=cytomegalovirus
CWD=chronic wasting disease
cy2=4'-6-diamidine-2-phenylindole
dsRed=red fluorescence protein
eGFP=enhanced green fluorescence protein
ELISA=enzyme linked immunoabsorbent assay
$F_{ab}$=antigen binding site of an antibody
$F_c$=constant region of an antibody
FFI=fatal familial insomnia
FITC=fluorescein isothiocyanate
FLAG=polypeptide consisting of the eight amino acids DYKDDDDK
GSS=Gerstmann-Straussler-Scheinker syndrome
GST=glutathione S-transferase
GST::LRP=fusion of GST (N-terminal) with LRP(C-terminal)
Igκ=κ-chain of the immunglobulin
i.p.=intraperitoneal
Jurkat cells=human, peripheral blood leukemia T cells
N1-47=scFv antibody selected from the naive scFv bank
His=histidine
HRP=horseradish peroxidase Linker=amino acid sequence which connects two protein domains
LR=67 kDa form of the laminin receptor (high affinity laminin receptor)
LRP=laminin receptor precursor
Mr(K)=molecular weight standard in kDa
pIII=phage coat protein
polyHis: polypeptide consisting of six histidine residues
$PrP^c$=cellular form of the prion protein
$PrP^{Sc}$=scrapie form of the prion proteins
S1-47=scFv antibody selected from the synthetic scFv bank
(Sc)GT1=(scrapie-infected) hypothalamic neuronal cells
(Sc)N2a=(scrapie-infected) neuroblastoma cells
W3=antibody W3 directed against LRP/LR, polyclonal
$scF_v$=single chain antibody of the variable region consisting of $V_L$ and $V_H$ connected by a linker
$scF_v$N3=single chain antibody N3 selected from the naive $scF_v$ bank
$scF_v$S18=single chain antibody S18 selected from the synthetic $scF_v$ bank
SFV=Semliki forest virus
TSE=transmissible spongiform encephalopathy
$V_L$=light chain of the variable region of an antibody
$V_H$=heavy chain of the variable region of an antibody The subject of a first aspect of the present invention is a single-chain antibody molecule, which is directed specifically against LRP/LR and which comprises the amino acid sequence SEQ ID No.2, and homologs or fragments thereof, and homologs of the fragments.

The subject of a further aspect of the present invention is a single-chain antibody molecule, which is directed specifically against LRP/LR and which comprises the amino acid sequence SEQ ID No. 4, and homologs or fragments thereof, and homologs of the fragments.

A homolog of the antibody molecule which comprises the amino acid sequence SEQ ID No. 2 or 4 is customarily homologous to at least 70%, preferably to 80 or 90% and in particular to 95%, to the antibody molecule comprising the amino acid sequence SEQ ID No. 2 or 4 over a region of at least 60, 80 or 100 or more adjacent amino acids.

In general, a fragment of the antibody molecule according to the invention which comprises the amino acid sequence SEQ ID No. 2 or 4, or a homolog thereof, has a sequence length of at least 30, 40, 50 or 60 amino acids.

In a preferred embodiment, the antibody molecule according to the invention is one having the designation S18, which has the amino acid sequence SEQ ID No. 2.

In a further preferred embodiment, the antibody molecule according to the invention is one having the designation N3, which has the amino acid sequence SEQ ID No. 4.

The single-chain antibodies (scFv) according to the invention consist of a fusion of the variable heavy chains ($V_H$) and the variable light chains ($V_L$) of an antibody molecule. Both chains are connected via a peptide linker (YOL). scFvs which originate from the scFv libraries carry a C-terminal histidine tag, which can be used both for the detection of the scFv and for its purification by means of IMAC (FIG. 1 and FIG. 2).

Antibodies against LRP/LR also serve as useful tools for the diagnosis of cancers and can also be employed as therapeutics in cancers. The single-chain antibodies described in the present application, preferably the antibody molecules having the designation S18 and N3, can also be employed for the diagnosis and therapy of cancers.

FIG. 10 shows the cell surface recognition and intracellular recognition of LRP/LR on Jurkat cells (human, peripheral blood leukemia T cells) by the single-chain antibodies S18 and N3. The example shows that the antibody molecules S18 and N3 preferred according to the invention can be suitable for the diagnosis of leukemia. From this finding, S18 and N3 can also be suitable for the diagnosis of other cancers.

Such antibodies are extremely suitable both for the diagnosis and for the therapy of transmissible spongiform encephalopathies (TSE). Therefore the single-chain antibodies described here for the first time are also suitable for the diagnosis of prion diseases.

The antibody molecules preferred according to the invention having the designation S18 or N3 were obtained from complex synthetic and naive antibody banks with the aid of phage-display technology using the GST::LRP fusion protein described in WO 98/53838 as a selection antigen.

The complex scFv banks used for the selection of the scFv antibodies together contained approximately $3 \times 10^9$ individual clones (the naive bank contained approximately $2 \times 10^9$ clones, the synthetic bank approximately $1 \times 10^9$ clones). The naive IgM bank was generated by the combination of the coding regions for the variable heavy and light chains after PCR amplification of the respective cDNA from spleen or PBLs (peripheral blood lymphocytes). For the production of the synthetic library, human scFv frameworks were selected which are distinguished by good folding and expression properties. The CDR3 sequences of the $V_H$ chain were randomized.

The affinity selection was carried out with each of the two banks on a GST::LRP fusion protein expressed in the Baculovirus system. The production of the GST::LRP fusion protein is described in WO 98/53838.

FIG. 2 schematically summarizes the generation of the $2 \times 10^9$ different clones for the naive bank. FIG. 3 summarizes the generation of the synthetic scFv antibody bank, which has a complexity of $1 \times 10^9$ clones.

FIG. 4 schematically summarizes the selection of scFv antibodies for specific binding to GST::LRP.

After the third selection round, crude periplasmatic extracts of 48 individual clones of in each case each bank were tested in the ELISA with respect to the recognition of the recombinant fusion protein GST::LRP (FIGS. 5 and 6). 66% of the individual clones in the case of the naive bank and 53% in the case of the synthetic bank showed a positive signal in the ELISA (FIG. 7).

Repeated testing on recombinant GST showed that all antibodies did not recognize GST, although the GST::LRP fusion protein was used as antigen (FIG. 7).

A restriction analysis of the DNAs coding for the scFv with BstNI identified one clone from the naive bank as highly enriched (FIG. 7). The CDR3 sequences of the clones which were enriched from the synthetic bank showed two different consensus sequences. All clones were tested in a Western Blot analysis with respect to the recognition of the recombinant GST::LRP fusion protein (FIG. 8). As a control, GST was added to each track, which showed that none of the clones recognized GST (FIG. 8).

Two clones having the designation N3 (from the naive bank) and S18 (from the synthetic bank) were selected on account of the very strong enrichment for further affinity purification on a $Cu^{2+}$ chelate column.

The single-chain antibody having the designation S18 is encoded at cDNA level from the DNA sequence SEQ ID No. 1.

The DNA is contained in the plasmid pEX/HAM/LRP-S18. The plasmid was deposited in the DSMZ, Mascheroder Weg 1b, D-38124 Brunswick under the number DSM 15962 on Oct. 2, 2003. After transformation in *E. coli* XL1-Blue, the production of the scFv antibody S18 is possible.

The single-chain antibody having the designation S18 shows at protein level the sequence SEQ ID No. 2.

The single-chain antibody having the designation N3 is encoded at cDNA level from the DNA sequence SEQ ID No. 3.

The DNA is contained in the plasmid pEX/HAM/LRP-N3. The plasmid was deposited in the DSMZ, Mascheroder Weg 1b, D-38124 Brunswick under the number DSM 15961 on Oct. 2, 2003. After transformation in *E. coli* XL1-Blue, the production of the scFv antibody N3 is possible.

The antibody having the designation N3 shows at protein level the sequence SEQ ID No. 4.

In a further embodiment according to the present invention, the antibody molecules according to the invention are further modified on one or more positions in order to increase the stability and/or in order to change their biochemical and/or biophysical properties.

The two single-chain antibodies S18 and N3 were tested in various biochemical and cell biology systems with respect to specific LRP/LR recognition.

Murine neuroblastoma cells (N2a) were tested by fluorescence-activated cell scanning (FACS) with the aid of the LRP/LR-specific antibody W3 (polyclonal) from WO 98/53838 and the scFv antibody S18 and N3 for cell surface expression of LRP/LR. N2a cells are the ideal cell system for the propagation of prions. FIG. 9 shows the detection of LRP/LR by the scFv antibodies S18 and N3 on the surface of N2a cells. This shows that both single-chain antibodies S18 and N3 specifically recognize LRP/LR on the surface of N2a cells.

The 37 kDa/67 kDa LRP/LR is strongly expressed on tumor tissue. For example, on the surface of metastasizing tumor cells (Coggin et al., 1999; Rohrer et al., 2001). FIG. 10 shows the detection of the 37 kDa/67 kDa LRP/LR in and on the surface of Jurkat cells with the aid of the scFv antibodies S18 and N3. Jurkat cells are human, peripheral blood leukemia T cells. This demonstrates that the single-chain antibodies described here are able to recognize LRP/LR on tumor cells and shows that the preferred antibodies according to the invention having the designation S18 and N3 are suitable for the diagnosis of cancer.

The scFv antibodies described here having the designation S18 and N3 are able to recognize recombinant human and murine 37 kDa/67 kDa LRP/LR in the fusion with a FLAG tag appended to the carboxy-terminus of LRP in baby hamster kidney cells transfected with recombinant Semliki forest virus RNA by Western Blotting, immunofluorescence and fluorescence-activated cell scanning (FACS). These methods are known to the person skilled in the art in the relevant specialty. FIG. 11 shows the recognition of the murine and human 37 kDa LRP::FLAGs and of the 67 kDa form by the scFv N3 and the recognition of the 37 kDa LRP::FLAG form by the scFv S18 in BHK cells by Western Blotting. FIG. 12 shows surface staining of human and murine LRP/LR-expressing BHK cells with the aid of the scFv antibodies S18 and N3. The polyclonal antibody W3 described in WO 98/53838 is likewise able in this respect. Both scFvs S18 and N3 likewise recognize both murine and human LRP/LR molecules on the surface of transfected BHK cells in the FACS analysis (FIG. 13). The examples shown demonstrate that scFv S18 and N3 recognize LRP/LR molecules highly specifically. The fact that various LRP/LR species of N3 and S18 are recognized is to be attributed to the extremely strong conservation of the protein during evolution (Ardini et al., 1998).

The subject of a further aspect of the present invention are diagnostic compositions which comprise an antibody molecule according to the invention in combination with an acceptable diluent and/or vehicle.

The preferred scFv antibodies according to the invention having the designation S18 and N3 can be employed as diagnostic tools for the recognition of transmissible spongiform encephalopathies. The antibody molecules having the designation S18 recognize, in the leucocyte fraction of the blood, and the antibody molecules having the designation S18 and N3 recognize, in the cerebrospinal fluid of cattle suffering from BSE, an increased level of the 67 kDa form of the laminin receptor (FIGS. 14 and 15). Both scFv antibodies serve as tools for a "surrogate marker test" for the recognition of BSE.

In contrast to the LRP/LR antibody W3 described in WO 98/53838, the single-chain antibodies S18 and N3 preferably used according to the invention are more specific for LR and are distinguished by a higher specificity on account of their monoclonal origin. Furthermore, both scFvs can be produced in unlimited amounts in *E. coli*, whereas the polyclonal antibody W3 is only available in limited amount.

In a similar manner, the antibody molecules preferably used according to the invention having the designation S18 and N3 can also be used for the diagnosis of TSEs other than BSE, such as scrapie in sheep, chronic wasting disease (CWD) in cervids, nvCJD, sCJD, fCJD, kuru, Gerstmann-Sträussler-Scheinker (GSS) syndrome and fatal familial insomnia (FFI) in man.

The subject of a further aspect of the present invention are pharmaceutical compositions which comprise an antibody molecule according to the invention in combination with a pharmaceutically acceptable diluent and/or vehicle.

The pharmaceutical composition according to the invention are suitable for the therapy of transmissible spongiform encephalopathies (TSEs). TSEs are understood as meaning all known forms of TSEs. The advantage of the antibody molecules according to the invention in comparison with the polyclonal W3 antibody described in WO 98/53838, or other monoclonal murine antibodies of identical specificity, lies in the human origin of the antibody molecules according to the invention and the low immunogenicity associated therewith. scFvs without the $F_c$ part and of human origin are, in consideration of the therapy of patients who are suffering from a TSE, of great advantage because of the potentially lower immunogenicity.

The antibody molecules according to the invention can be employed for the prevention of the binding and internalization of prion proteins to its 37 kDa/67 kDa laminin receptor (see FIG. 16).

Furthermore, the antibody molecules according to the invention can be employed for the treatment of cells infected with scrapie, such as ScGT1, ScN2a and other brain cells which can be infected with scrapie (FIG. 17). Furthermore, the antibody molecules according to the invention can also be employed for prevention (FIG. 18). In this embodiment, they should prevent the outbreak of a prion disease in cell culture.

In a further embodiment, the antibody molecules according to the invention can be employed in vivo in animals in order to cure animals such as rodents (hamsters, mice) of a prion infection or of a transmissible spongiform encephalopathy. Initially, as detailed in FIG. 19, possible side effects of the antibody molecules according to the invention are evaluated by injecting the antibody molecules according to the invention into healthy mice or hamsters. Injection is carried out subcutaneously or directly into the brain. The various possibilities of injection of antibodies in mammals are familiar to the person skilled in the art. Side effects of the antibodies are monitored after certain times post-injection up to the end of the life of the mouse (about 800 days). In a further embodiment such as is shown in FIG. 19, the antibodies according to the invention are injected into the rodents at certain times after inoculation of the rodents with $PrP^{Sc}$. A possible delay in the outbreak of a TSE or a prevention of a TSE outbreak is observed by the analysis of the dead-time of the $PrP^{Sc}$ accumulation (brain+spleen) and by carrying out psychomotor tests. These methods are known to the person skilled in the art in the relevant specialty.

The subject of a further aspect of the present invention is the use of the antibodies according to the invention in the context of gene therapy and cell therapy (FIG. 20). The gene therapy approach introduces the genes which code for the antibody molecules according to the invention into the organism to be treated. A number of strategies have so far been monitored for gene transfer to neuronal cells using viral vectors (lentiviruses, adenoviruses, adeno-associated viruses (AAV). In this case, the adeno-associated virus (AAV) system was the most promising. AAV is nonpathogenic and can infect nondividing cells such as neurones.

Gene transfer with AAV to the central nervous system (CNS) is efficient and takes place without activation of the cellular or humoral immune response. Gene transfer with AAV was achieved in various animal systems of neurological dysfunction, such as Parkinson's disease (Kirik et al., 2002; Mandel et al., 1997), Alzheimer's disease (Klein et al., 2000), demyelining disease (multiple sclerosis) (Guy et al., 1998), and was also successful for the treatment of brain tumors (Ma et al., 2002).

In a further embodiment, the antibody molecules according to the invention can be expressed in the brain by recombinant AAV viruses. Among the AAV serotypes, AAV2 is the most highly adapted and preferentially transduces neuronal cells. An AAV vector, preferentially an AAV-2 vector which codes for the antibody molecules according to the invention, is used in order to produce high-titre virions according to the method of Grimm (Grimm et al., 1998). 293 cells (human embryonic kidney cell line) are cotransfected with the AAV vector, which codes for an antibody molecule according to the invention, together with an AAV helper plasmid (pDG), which expresses the AAV coat protein genes and further adeno-associated virus genes, which are necessary for helper functions in packaging. Neuronal cells infected with scrapie (ScGT1, ScN2a and further brain cells infected with scrapie) are infected with recombinant AAV viruses, which express the antibody molecules according to the invention, in order to show that the viruses can cure the cells of scrapie (FIG. 21). The recombinant AAV viruses are then injected into the brain of mice, preferably C57Bl6 (FIG. 22). The expression of the antibody molecules according to the invention is checked at various times after the infection by means of Western Blot analysis of the brain fraction (FIG. 22A). Recombinant AAV viruses are injected at various times before and after inoculation with $PrP^{Sc}$ (FIG. 22B). A delay in the outbreak of a TSE disease of the mice is determined by psychomotor tests and histological and immunohistochemical analysis of the brain.

The subject of a further embodiment of the present invention are pharmaceutical compositions which comprise cells producing the antibody molecules according to the invention, the pharmaceutical compositions being suitable to be introduced directly into the brain of mammals. For example, these pharmaceutical compositions can be capsules which contain the antibody-producing cells according to the invention. These compositions are used to treat mammals, including man, which are suffering from a TSE. This strategy implies using genetically modified cells which are able to secrete a protein, in the present case the antibody molecules according to the invention (FIG. 20). The cells are encapsulated in an immunoprotective polymer, e.g. cellulose sulfate, whose pores allow it to release large molecules, as in the present case antibody. In this process, the cells remain alive over a long period. For a summary of this technique, see also the article by Pelegrin et al., 1998. This strategy has already been employed successfully for the treatment of murine viral diseases (Pelegrin et al., 2000) and human diseases in an animal model such as Parkinson's disease in primates (Date et al., 2000) and Huntington's disease in rats (Emerich et al., 1996).

This process requires the following steps: neuroblastoma cells or other neuronal cells (PC 12) are transiently or stably transfected with an expression vector such as, for example, pSecTag2 (FIG. 23). For secretion, the Ig-κ chain leader sequence is used. For expression in neuronal cells promoters are used, such as CMV (cytomegalovirus). The secretion of the antibodies according to the invention from N2a cells has already been detected (FIG. 23), which demonstrates that the process functions with the antibodies according to the invention. With scrapie-infected neuronal cells, transfection is furthermore carried out using the secretion vectors according to the invention. Owing to the secretion of both antibodies from these cells, the cells can be cured of scrapie (FIG. 24).

For the transplantation of encapsulated cells into the brain of mammals including man for the therapy of TSEs, muscle cells (preferably C2.7 cells) are used, since these are able to secrete antibody over a long period of time if they are transplanted into mice. Myoblasts or differentiated muscle cells (preferably C2.7 cells) are stably transfected with an expression vector which expresses the antibody according to the invention under the control of a muscle cell-specific promoter (FIG. 23). Alternatively, neuronal cells (PC12 cells) or baby hamster kidney (BHK) cells or NIH3T3 cells can also be used, which can secrete the antibodies according to the invention, for further encapsulation and transplantation. The cells expressing the antibody molecules according to the invention are encapsulated in the manner known to the person skilled in the art in the relevant specialty. The process is described in the summary in Pelegrin et al., 1998 (Pelegrin et al., 1998). The material used here can be, for example, cellulose sulfate (Pelegrin et al., 1998).

The encapsulated cells are transplanted into brains of mice in the manner known to the person skilled in the art in this specialty. As in the case of the gene therapy approach described above with AAV viruses, initially the expression of the single-chain antibody is tested. In order to check the therapeutic effect of the antibodies according to the invention against a TSE disease, the experimental animals, preferably mice or hamsters, transplanted with cells expressing the antibody molecules according to the invention are inoculated with $PrP^{Sc}$. A delay in the outbreak of a TSE disease of the mice is determined by psychomotor tests and histological and immunohistochemical analysis of the brain.

The present invention is explained in greater detail below with the aid of nonrestricting examples with reference to the drawings.

EXAMPLES

Example 1

Selection of the scFv S18 and N3 from synthetic and naive scFv banks (biopanning)

The antigen used for the selection of single-chain scFv fragments was the GST::LRP fusion protein described in WO 98/53838.

For the selection of the scFv antibodies, two complex scFv banks were used which contained approximately $3 \times 10^9$ individual clones (the naive bank contained approximately $2 \times 10^9$ clones, the synthetic bank approximately $1 \times 10^9$ clones). The naive IgM bank was generated by the combination of the coding regions for the variable heavy and light chains after PCR amplification of the respective cDNA from spleen or PBLs (peripheral blood lymphocytes). For the preparation of the synthetic library, human scFv frameworks were selected which were distinguished by good folding and expression properties. The CDR3 sequences of the $V_H$ chain were randomized.

The selection was carried out with each of the two banks on a GST::LRP fusion protein expressed in the Baculovirus system. The production of the GST::LRP fusion protein is described in WO 98/53838.

FIG. 2 summarizes schematically the generation of the $2 \times 10^9$ different clones for the naive bank. FIG. 3 summarizes the generation of the synthetic scFv antibody bank, which shows a complexity of $1 \times 10^9$ clones.

FIG. 4 summarizes schematically the selection of scFv antibodies for specific binding to GST::LRP.

After the third selection round, periplasmatic crude extracts of 48 individual clones of in each case each bank were tested in the ELISA with respect to the recognition of the recombinant fusion protein GST::LRP (FIGS. 5 and 6). 66% of the individual clones in the case of the naive bank and 53% in the case of the synthetic bank showed a positive signal in the ELISA (FIG. 7).

Repeated testing on recombinant GST showed that all antibodies did not recognize GST, although the antigen used was the GST::LRP fusion protein (FIG. 7).

A restriction analysis of the DNAs coding for the scFv with BstNI showed one clone from the naive bank as highly enriched (FIG. 7). The $V_H$-CDR3 sequences of the clones isolated from the synthetic bank show two different consensus sequences. All clones were tested in a Western Blot analysis with respect to the recognition of the rec. GST::LRP fusion protein (FIG. 8). The control employed was GST, which showed that none of the clones recognized GST (FIG. 8).

Two clones having the designation N3 (from the naive bank) and S18 (from the synthetic bank) were selected on account of the strongest enrichment for further affinity purification on a $Cu^{2+}$ chelate column.

The single-chain antibody S18 is encoded at cDNA level by the DNA sequence SEQ ID No. 1.

The DNA is contained in the plasmid pEX/HAM/LRP-S18. The plasmid was deposited in the DSMZ, Mascheroder Weg 1b, D-38124 Brunswick under the number DSM 15962 on Oct. 2, 2003. After transformation in E. coli XL1-Blue, the production of the scFv antibody S18 is possible.

At protein level, the S18 antibody shows the sequence SEQ ID No. 2.

The single-chain antibody N3 is encoded at cDNA level by the DNA sequence SEQ ID No. 3.

The DNA is contained in the plasmid pEX/HAM/LRP-N3. The plasmid was deposited in the DSMZ, Mascheroder Weg 1b, D-38124 Brunswick under the number DSM 15961 on Oct. 2, 2003. After transformation in E. coli XL1-Blue, the production of the scFv antibody N3 is possible.

At protein level, the N3 antibody shows the sequence SEQ ID No. 4.

The person skilled in the art in the relevant specialty can be expressed the scFv antibodies S18 and N3 in a manner known per se by transformation of the plasmids pEX/HAM/LRP-S18 and pEX/HAM/LRP-N3 in E. coli strains such as XL1-Blue in large amounts. The person skilled in the art in the relevant specialty can be purified the expressed proteins S18 and N3 by IMAC (immobilized metal affinity chromatography) in a manner known per se.

Alternatively, the scFv antibodies S18 and N3 can be expressed in the E. coli strain RV308. To this end, the cDNA from the plasmids pEX/HAM/LRP-S18 and pEX/HAM/LRP-N3 coding for S18 and N3 is cloned in the vector pSKK-2 by means of NcoI/NotI, which led to the expression plasmids pSKK-S-2-18 and pSKK-2-N3.

The expression of the scFv S18 and N3 from pSKK-2 involves the advantage that PIII fusion protein is no longer produced. Moreover, the chaperone SKP is expressed by pSKK-2, which contributes to the improvement of the protein folding. Furthermore, an additional c-myc tag is introduced at the C-terminus, which additionally makes possible alternative detection by means of an anti-c-myc antibody. The advantage of the RV308 compared with XL1-Blue is its more rapid growth.

For the expression of the scFv antibodies S18 and N3, overnight cultures of E. coli RV308 are transformed with pSKK-S18/N3 (2YT medium containing 100 µg/ml of ampicillin and 50 mM glucose). Dilution of the culture 1:10 in 2YT Medium with 100 µg/ml ampicillin and 50 mM glucose, and culturing until an $OD_{600}$ of 0.6-0.8 is reached follows (26° C., 160 rpm, about 2 h). The culture is centrifuged at 7500 rpm, 20° C., for 20 min. The pellet is resuspended in 1 vol of YTBS with 100 µg/ml of ampicillin, 0.2 mM IPTG. Incubation overnight at 21° C., 160 rpm follows. Centrifugation at 9000 rpm, 4° C., for 20 min then follows. The pellet is resuspended in 1/20 vol with cold TES buffer. Incubation for 1 h on ice with occasional shaking follows. Centrifugation at 9000 rpm, 4° C., for 1 h. The supernatant is dialyzed overnight against PBS (4° C.). The dialyzed antibody solution is centrifuged at 9000 rpm, 4° C., for 1 h. The antibodies S18 and N3 are purified by means of IMAC (immobilized metal affinity chromatography). The antibodies S18 and N3 are bound to "chelating sepharose" beads overnight at 4° C. The beads are washed with dialysis buffer at 4° C., and washing of the beads with wash buffer at 4° C. follows. The scFvs S18 and N3 are eluted with elution buffer (imidazble) at 4° C. The analysis of the scFv antibodies S18 and N3 on a 12% strength SDS PA gel stained with Coomassie Blue shows bands at a level of approximately 30 kDa. After blotting the bands on a PVDF membrane, it was possible to detect both scFv antibodies by means of anti-c-myc and anti-His antibodies.

The scFv antibodies S18 and N3 thus produced can be employed for further applications in the following examples.

Example 2

Characterization of the scFv antibodies S18 and N3 on cultured cells by FACS, IF and Western Blotting—detection of an increased LRP/LR level on tumor cells (Jurkat cells)

Murine neuroblastoma cells (N2a) were tested for cell surface expression of LRP/LR by fluorescence-activated cell scanning (FACS) with the aid of the LRP/LR specific antibody W3 (polyclonal) from WO 98/53838 and the scFv antibodies S18 and N3 (FIG. 9). N2a cells are the ideal cell system for the propagation of prions. FIG. 9 shows the detection of LRP/LR by the scFv antibodies S18 and N3 on the surface of N2a cells. This shows that both single-chain antibodies S18 and N3 specifically recognize LRP/LR on the surface of N2a cells. Technical details can be inferred from the legend to FIG. 9.

The 37 kDa/67 kDa LRP/LR is strongly expressed on tumor tissue, for example on the surface of the metastasizing tumor cells (Coggin et al., 1999; Rohrer et al., 2001). FIG. 10 shows the detection of the 37 kDa/67 kDa LRP/LR in and on the surface of Jurkat cells with the aid of the scFv antibodies S18 and N3. Jurkat cells are human, peripheral blood leukemia T cells. This demonstrates that the single-chain antibodies described here are able to recognize LRP/LR on tumor cells and shows that the antibodies S18 and N3 are suitable for the diagnosis of cancer. Technical details can be inferred from the legend to FIG. 10.

The scFv antibodies S118 and N3 described here are able to recognize recombinant human and murine 37 kDa/67 kDa LRP/LR in the fusion with a FLAG tag appended to the carboxy terminus of LRP in baby hamster kidney cells transfected with rec. Semliki forest virus RNA by Western Blotting, immunofluorescence and fluorescence-activated cell scanning (FACS). These methods are known to the person skilled in the art in the relevant specialty. FIG. 11 shows the recognition of the murine and human 37 kDa LRP::FLAGs and the 67 kDa form by the scFv N3 and the recognition of the 37 kDa LRP::FLAG form by the scFv S18 in BHK cells by Western Blotting. FIG. 12 shows a surface stain of human and murine LRP/LR-expressing BHK cells with the aid of the scFv antibodies S18 and N3. The polyclonal antibody W3 described in WO 98/53838 is likewise able to do this. Both scFvs S18 and N3 likewise recognize both murine and human LRP/LR molecules on the surface of transfected BHK cells in the FACS analysis (FIG. 13). The examples shown demonstrate that scFv S18 and N3 LRP/LR recognize molecules highly specifically. The fact that the various LRP/LR species of N3 and S18 are recognized is attributed to the extremely strong conservation of the protein during evolution (Ardini et al., 1998).

Technical details can be inferred from the legends to FIGS. 11, 12 and 13.

Example 3

Application of svFv Antibodies S18 and N3 in BSE Diagnosis

The scFv antibodies S18 and N3 can are to be employed as diagnostic tools for the recognition of transmissible spongiform encephalopathies. It is demonstrated here that scFv S18 in the leucocyte fraction of the blood and scFv S18 and N3 in the cerebrospinal fluid of cattle suffering from BSE can recognize an increased level of the 67 kDa form of the laminin receptor (FIGS. 14 and 15). Both scFv antibodies serve as tools for a "surrogate marker test" for the recognition of BSE. In contrast to the LRP/LR antibody W3 described in WO 98/53838, the single-chain antibodies S18 and N3 are more specific for LR and are distinguished by a higher specificity on account of their monoclonal origin. Furthermore, both scFv can be produced in unlimited amount in $E.\ coli$, whereas the polyclonal antibody W3 is only available in limited amount. A great advantage compared with monoclonal antibodies from experimental animals consists in the human origin of the isolated scFv molecules.

Technical details can be inferred from the legends to FIGS. 14 and 15.

Example 4

Application of svFv Antibodies S18 and N3 in TSE Therapy

It is claimed that the single-chain antibodies scFv S18 and N3 to be employed for the therapy of transmissible spongiform encephalopathies (TSEs). TSEs are understood as meaning all known forms of TSEs. The advantage of scFv S18 and N3 in comparison with the polyclonal W3 antibody described in WO 98/53838 or other monoclonal murine antibodies of identical specificity lies in the human origin of the scFvs and the low immunogenicity associated therewith. ScFv without an $F_c$ part and of human origin are of great advantage in consideration of the therapy of patients who are suffering from a TSE because of the potentially lower immunogenicity. Moreover, in contrast to W3, the scFvs can be produced in large amount.

scFv S18 and N3 should prevent the binding and internalization of prion proteins to their 37 kDa/67 kDa laminin receptor—as described in FIG. 16.

The scFv S18 and N3 should be employed for the treatment of scrapie-infected cells such as ScGT1, ScN2a and other scrapie-infectable brain cells (FIG. 17). Furthermore, the scFv S18 and N3 antibodies can also be employed for prevention (FIG. 18). In this embodiment, they should also prevent the outbreak of a prion disease in cell culture.

The scFvs S18 and N3 should be employed in vivo in animals in order to cure animals such as rodents (hamsters mice) from a prion infection or a transmissible spongiform encephalopathy. Initially, as detailed in FIG. 19, possible side effects of the ScFv antibodies S18 and N3 are evaluated by injecting the scFv antibodies S18 and N3 into healthy mice or hamsters. Injection is carried out intraperitoneally. The various possibilities of injection of antibodies into mammals are familiar to the person skilled in the art. Side effects of the antibodies are monitored after certain times post-injection up to the end of the life of the mouse (about 800 days). In a further embodiment as shown in FIG. 19, the ScFv antibodies are injected into the rodents intraperitoneally at certain times after an intraperitoneal inoculation of the rodents with $PrP^{Sc}$. Protocol: An initial dose of in each case 200 μg of the S18 and N3 antibodies is injected intraperitoneally (i.p.) into preferably C57/BL6 mice one day after intraperitoneal inoculation with a prion strain, preferably the BSE strain 6PB1. I.p. injections twice per week with 100 μg of scFv S18/N3 for a further preferably eight weeks follow. Some of the animals are sacrificed 90 days p.i. and investigated biochemically for $PrP^{Sc}$ presence. The other animals are either investigated for the terminal stage of a TSE disease or, if no symptoms occurred, at the end of their lifetime. A possible delay in the outbreak of a TSE or a prevention of a TSE outbreak is observed by the analysis of the times of death, the $PrP^{Sc}$ accumulation (brain+spleen) and by carrying out psychomotor tests. These methods are known to the person skilled in the art in the relevant specialty.

scFv antibodies S18 and N3 should be transferred in vivo by means of gene therapy and cell therapy (FIG. 20). The gene therapy approach introduces the genes which code for the scFvs into the organism to be treated. A number of strategies have so far been monitored for gene transfer to neuronal cells using viral factors (lentiviruses, adenoviruses, adeno-associated viruses (AAV)). In this case, the adeno-associated-virus (AAV) system was the most promising. AAV is nonpathogenic and can infect nondividing cells such as neurones. Gene transfer with AAV into the central nervous system (CNS) is efficient and takes place without activation of the cellular or humoral immune response. Gene transfer with AAV is achieved in various animal systems of neurological dysfunctions, such as Parkinson's disease (Kirik et al., 2002; Mandel et al., 1997), Alzheimer's disease (Klein et al., 2000), demyelining disease (multiple sclerosis) (Guy et al., 1998), and was also successful for the treatment of brain tumors (Ma et al., 2002).

The scFvs S18 and N3 should be expressed in the brain by rec. AAV viruses. Among the AAV serotypes, AAV2 is the most highly adapted and preferentially transduces neuronal cells. An AAV vector, preferentially an AAV-2 vector, which codes for the scFv S18 or N3, is used in order to produce high-titer virions according to the method of Grimm (Grimm et al., 1998): 293 cells (human embryonic kidney cell line) are cotransfected with the AAV vector, which encodes S18 and N3, together with an AAV helper plasmid (pDG), which expresses the AA coat protein genes and further adeno-associated virus genes, which are necessary for helper functions in packaging. Scrapie-infected neuronal cells (ScGT1, ScN2a and further scrapie-infected brain cells) are infected with recombinant AAV viruses which express scFv S18 and N3 in order to show that the viruses can cure the cells of scrapie (FIG. 21). The recombinant AAV viruses are then injected into the brain of mice, preferably C57B16 (FIG. 22). The expression of scFvs S18 and N3 is checked at various times after infection by means of Western Blot analysis of the brain fraction (FIG. 22A). Rec. AAV viruses are injected at different times before and after inoculation with $PrP^{Sc}$ (FIG. 22B). A delay in the outbreak of a TSE disease in the mice is determined by psychomotor tests and histological and immunohistochemical analysis of the brain.

scFv antibodies S18 and N3 should be introduced directly into the brain of mammals by transplanting capsules which contain antibody-producing cells. This embodiment likewise serves for treating mammals, including man, which are suffering from a TSE. This strategy implies using genetically modified cells which are able to secrete a protein, in the present case the scFv antibodies S18 and N3 (FIG. 20). The cells are encapsulated in an immunoprotective polymer, e.g. cellulose sulfate, whose pores allow it to release large molecules, as in the present case antibodies. In this case the cells remain alive for a long time. For a summary of this technique see (Pelegrin et al., 1998). This strategy has already been employed successfully for the treatment of murine viral diseases (Pelegrin et al., 2000) and human diseases in an animal model such as Parkinson's disease in primates (Date et al., 2000) and Huntington's disease in rats (Emerich et al., 1996).

This process necessitates the following steps: Neuroblastoma cells or other neuronal cells (PC 12) are transiently or stably transfected with an expression vector such as, for example, pSecTag2 (FIG. 23). For secretion, the Ig-κ chain leader sequence is used. For expression in neuronal cells promoters are used, such as CMV (cytomegalovirus). The secretion of the antibodies S18 and N3 from N2a cells has already been detected (FIG. 23), which demonstrates that the process works with the scFv antibodies S18 and N3. Scrapie-infected neuronal cells are furthermore transfected with the S18/N3 secretion vectors. By means of the secretion of both antibodies from these cells, the cells can be cured of scrapie (FIG. 24).

For the transplantation of encapsulated cells into the brain of mammals including man for the therapy of TSEs, muscle cells (preferably C2.7 cells) are used, since these are able to secrete antibodies over a long period of time when they are transplanted into mice. Myoblasts or differentiated muscle cells (preferably C2.7 cells) are stably transfected with an expression vector which expresses the scFv antibodies S18 or N3 under the control of a muscle cell-specific promoter (FIG. 23). Alternatively, neuronal cells (PC12 cells) or baby hamster kidney (BHK) cells or NIH3T3 cells which can secrete the antibody S18/N3 can also be used for further encapsulation and transplantation. The scFv S18/N3-expressing cells are encapsulated in the manner known to the person skilled in the art in the relevant specialty. The process is described in summary in Pelegrin et al., 1998 (Pelegrin et al., 1998). The material used here can be, for example, cellulose sulfate (Pelegrin et al., 1998).

The encapsulated cells are transplanted into the brains of mice in the manner known to the person skilled in the art in this specialty. As in the case of the gene therapy approach with AAV viruses described above, the expression of the single-chain antibodies is initially tested. In order to check the therapeutic effect of the scFv antibodies against a TSE disease, the experimental animals transplanted with scFv S18/N3 are preferably mice or hamsters inoculated with $PrP^{Sc}$. A delay in the outbreak of a TSE disease in the mice is determined by psychomotor tests and histological and immunochemical analysis of the brain.

The person skilled in the art in the relevant specialty is familiar with the techniques for the details in Example 4.

Example 5

Epitope Mapping of scFvs S18 and N3

This technique is used to identify the epitopes on LRP which are recognized by the scFvs S18 and N3. To this end, 92 different peptides were synthesized, which in each case had a length of 15 amino acids. The N-terminus of each peptide was displaced by 3 amino acids in relation to the previous peptide, so that each peptide overlapped with the previous peptide by 12 amino acids. The synthesis of the peptides was carried out on a cellulose membrane.

As shown in FIG. 26, three strong signals were detected with the antibody S18. These correspond to the peptides EKAVTKEEFQGEWTA, VTKEEFQGEWTAPAP, and EEFQGEWTAPAPEFT. The common epitope is EEFQGEWTA (AA225-234). This means to the person skilled in the art that the epitope on LRP for the scFv S18 could extend from amino acid 225 to 243 on the laminin receptor. This is illustrated schematically in FIG. 27.

Using the antibody N3, four signals were visualized, as shown in FIG. 26: PSVPIQQFPTEDWSA, PIQQFP TEDWSAAPT, QFPTEDWSAAPTAQA and TEDWSAAPTAQATEW. Here, the common epitope is TEDWSA (AA261-266). This means to the person skilled in the art that the epitope on LRP for the scFv N3 could extend from amino acid 261 to 266 on the laminin receptor (cf. FIG. 27).

The techniques for the details in Example 5, which are familiar to the person skilled in the art in the relevant specialty, are explained below in detail.

The antibody binding test was carried out similarly to Western Blots for the detection of LRP by the antibodies scFv S18 and N3 (Cf. FIG. 11). In this case, the membrane bound with 92 peptides was incubated with the scFv antibodies S18 and N3 (dilution 1:5000). In order to remove an antibody (S18) (in order to detect with the second antibody (N3)), the membrane was incubated 3 times at 60° C. for 20 minutes with "stripping" buffer (8 M urea, 0.5% β-mercaptoethanol).

BIBLIOGRAPHY

Aguzzi, A. and Weissmann, C. (1998) Prion diseases. *Haemophilia,* 4, 619-627.

Ardini, E., Pesole, G., Tagliabue, E., Magnifico, A., Castronovo, V., Sobel, M. E., Colnaghi, M. I. and Menard, S. (1998) The 67-kDa laminin receptor originated from a ribosomal protein that acquired a dual function during evolution. *Mol. Biol. Evol.,* 15, 1017-1025.

Auth, D. and Brawerman, G. (1992) A 33-kDa polypeptide with homology to the laminin receptor: component of translation machinery. *Proc Natl Acad Sci USA,* 89, 4368-4372.

Beck, K., Hunter, I. and Engel, J. (1990) Structure and function of laminin: anatomy of a multidomain glycoprotein. *FASEB J.*, 4, 148-160.

Buto, S., Tagliabue, E., Ardini, E., Magnifico, A., Ghirelli, C., van den Brule, F., Castronovo, V., Colnaghi, M. I., Sobel, M. E. and Menard, S. (1998) Formation of the 67-kDa laminin receptor by acylation of the precursor. *J. Cell. Biochem.*, 69, 244-251.

Canfield, S. M. and Khakoo, A. Y. (1999) The nonintegrin laminin binding protein (p67 LBP) is expressed on a subset of activated human T lymphocytes and, together with the integrin very late activation antigen-6, mediates avid cellular adherence to laminin. *J Immunol*, 163, 3430-3440.

Castronovo, V., Claysmith, A. P., Barker, K. T., Cioce, V., Krutzsch, H. C. and Sobel, M. E. (1991) Biosynthesis of the 67 kDa high affinity laminin receptor. *Biochem. Biophys. Res. Commun.*, 177, 177-183.

Coggin, J. H., Jr., Barsoum, A. L. and Rohrer, J. W. (1999) 37 kiloDalton oncofetal antigen protein and immature laminin receptor protein are identical, universal T-cell inducing immunogens on primary rodent and human cancers. *Anticancer Res*, 19, 5535-5542.

Date, I., Shingo, T., Yoshida, H., Fujiwara, K., Kobayashi, K. and Ohmoto, T. (2000) Grafting of encapsulated dopamine-secreting cells in Parkinson's disease: long-term primate study. *Cell Transplant*, 9, 705-709.

Davis, S. C., Tzagoloff, A. and Ellis, S. R. (1992) Characterization of a yeast mitochondrial ribosomal protein structurally related to the mammalian 68-kDa high affinity laminin receptor. *J Biol Chem*, 267, 5508-5514.

Douville, P. J. and Carbonetto, S. (1992) Genetic linkage analysis in recombinant inbred mice of P40, a putative clone for the high-affinity laminin receptor. *Mamm. Genome*, 3, 438-446.

Emerich, D. F., Lindner, M. D., Winn, S. R., Chen, E. Y., Frydel, B. R. and Kordower, J. H. (1996) Implants of encapsulated human CNTF-producing fibroblasts prevent behavioral deficits and striatal degeneration in a rodent model of Huntington's disease. *J Neurosci*, 16, 5168-5181.

Enright, A. J., Van Dongen, S. and Ouzounis, C. A. (2002) An efficient algorithm for large-scale detection of protein families. *Nucleic Acids Res*, 30, 1575-1584.

Fernandez, M.-T., Castronovo, V., Rao, C. N. and Sobel, M. E. (1991) The high affinity murine laminin receptor is a member of a multicopy gene family. *Biochem. Biophys. Res. Commun.*, 175, 84-90.

Garcia-Hernandez, M., Davies, E. and Staswick, P. E. (1994) *Arabidopsis* p40 homologue. A novel acidic protein associated with the 40 S subunit of ribosomes. *J. Biol. Chem.*, 269, 20744-20749.

Gauczynski, S., Hundt, C., Leucht, C. and Weiss, S. (2001 a) Interaction of prion proteins with cell surface receptors, molecular chaperones and other molecules. *Adv. Prot. Chem.*, 57, 229-272.

Gauczynski, S., Krasemann, S., Bodemer, W. and Weiss, S. (2002) Recombinant human prion protein mutants huPrP D178N/M129 (FFI) and huPrP+90R (fCJD) reveal proteinase K resistance. *J Cell Sci*, 115, 4025-4036.

Gauczynski, S., Peyrin, J. M., Haik, S., Leucht., C., Hundt, C., Rieger, R., Krasemann, S., Deslys, J. P., Dormont, D., Lasmezas, C. I. and Weiss, S. (2001b) The 37-kDa/67-kDa laminin receptor acts as the cell-surface receptor for the cellular prion protein. *EMBO J*, 20, 5863-5875.

Grimm, D., Kern, A., Rittner, K. and Kleinschmidt, J. A. (1998) Novel tools for production and purification of recombinant adenoassociated virus vectors. *Hum Gene Ther*, 9, 2745-2760.

Guy, J., Qi, X. and Hauswirth, W. W. (1998) Adeno-associated viral-mediated catalase expression suppresses optic neuritis in experimental allergic encephalomyelitis. *Proc Natl Acad Sci USA*, 95, 13847-13852.

Hinek, A., Wrenn, D. S., Mecham, R. P. and Barondes, S. H. (1988) The elastin receptor: a galactoside binding protein. *Science*, 239, 1539-1541.

Hundt, C., Peyrin, J. M., Haik, S., Gauczynski, S., Leucht, C., Rieger, R., Riley, M. L., Deslys, J. P., Dormont, D., Lasmezas, C. I. and Weiss, S. (2001) Identification of interaction domains of the prion protein with its 37-kDa/67-kDa laminin receptor. *EMBO J*, 20, 5876-5886.

Jackers, P., Clausse, N., Fernandez, M., Berti, A., Princen, F., Wewer, U., Sobel, M. E. and Castronovo, V. (1996a) Seventeen copies of the human 37 kDa laminin receptor precursor/p40 ribosome-associated protein gene are processed pseudogenes arisen from retropositional events. *Biochim. Biophys. Acta*, 1305, 98-104.

Jackers, P., Minoletti, F., Belotti, D., Clausse, N., Sozzi, G., Sobel, M. E. and Castronovo, V. (1996b) Isolation from a multigene family of the active human gene of the metastasis-associated multifunctional protein 37LRP/p40 at chromosome 3p21.3. *Oncogene*, 13, 495-503.

Keppel, E. and Schaller, H. C. (1991) A 33 kDa protein with sequence homology to the 'laminin binding protein' is associated with the cytoskeleton in hydra and in mammalian cells. *J. Cell. Science*, 100, 789-797.

Kinoshita, K., Kaneda, Y., Sato, M., Saeki, Y., Wataya, K. M. and Hoffmann, A. (1998) LBP-p40 binds DNA tightly through associations with histones H2A, H2B, and H4. *Biochem Biophys Res Commun*, 253, 277-282.

Kirik, D., Georgievska, B., Burger, C., Winkler, C., Muzyczka, N., Mandel, R. J. and Bjorklund, A. (2002) Reversal of motor impairments in parkinsonian rats by continuous intrastriatal delivery of L-dopa using rAAV-mediated gene transfer. *Proc Natl Acad Sci USA*, 99, 4708-4713.

Klein, R. L., Hirko, A. C., Meyers, C. A., Grimes, J. R., Muzyczka, N. and Meyer, E. M. (2000) NGF gene transfer to intrinsic basal forebrain neurons increases cholinergic cell size and protects from age-related, spatial memory deficits in middle-aged rats. *Brain Res*, 875, 144-151.

Landowski, T. H., Dratz, E. A. and Starkey, J. R. (1995) Studies of the structure of the metastasis-associated 67 kDa laminin binding protein: fatty acid acylation and evidence supporting dimerization of the 32 kDa gene product to form the mature protein. *Biochemistry*, 34, 11276-11287.

Lasmézas, C. I. and Weiss, S. (2000) Molecular Biology of Prion Diseases. In Cary, J. W., Linz, J. E. and Bhatnagar, D. (eds.), *Microbial Foodborne Diseases. Mechanisms of Pathogenicity and Toxin Synthesis*. Technomic Publishing CO., INC, Lancaster (USA), pp. 495-537.

Lesot, H., Kühl, U. and von der Mark, K. (1983) Isolation of a laminin binding protein from muscle cell membranes. *EMBO J*, 2, 861-865.

Leucht, C., Simoneau, S., Rey, C., Vana, K., Rieger, R., Lasmezas, C. I. and Weiss, S. (2003) The 37 kDa/67 kDa laminin receptor is required for PrP(Sc) propagation in scrapie-infected neuronal cells. *EMBO Rep*, 4, 290-295.

Leucht, C. and Weiss, S. (2002) Der Prion Protein Rezeptor. *Nova Acta Leopoldina*, 87, 39-54.

Lopez-Ribot, J. L., Casanova, M., Monteagudo, C., Sepulveda, P. and Martinez, J. P. (1994) Evidence for the presence of a high-affinity laminin receptor-like molecule on the surface of *Candida albicans* yeast cells. *Infect Immun*, 62, 742-746.

Ludwig, G. V., Kondig, J. P. and Smith, J. F. (1996) A putative receptor for Venezuelan equine encephalitis virus from mosquito cells. *J Virol*, 70, 5592-5599.

Ma, H. I., Lin, S. Z., Chiang, Y. H., Li, J., Chen, S. L., Tsao, Y. P. and Xiao, X. (2002) Intratumoral gene therapy of malignant brain tumor in a rat model with angiostatin delivered by adeno-associated viral (AAV) vector. *Gene Ther*, 9, 2-11.

Malinoff, H. L. and Wicha, M. S. (1983) Isolation of a cell surface receptor for laminin from murine fibrosarcoma cells. *J. Cell. Biol.*, 96, 1475-1479.

Mandel, R. J., Spratt, S. K., Snyder, R. O. and Leff, S. E. (1997) Midbrain injection of recombinant adeno-associated virus encoding rat glial cell line-derived neurotrophic factor protects nigral neurons in a progressive 6-hydroxy-dopamine-induced degeneration model of Parkinson's disease in rats. *Proc Natl Acad Sci USA*, 94, 14083-14088.

Mecham, R. P. (1991) Receptors for laminin on mammalian cells. *FASEB J*, 5, 2538-2546.

Melnick, M. B., Noll, E. and Perrimon, N. (1993) The *Drosophila* stubarista phenotype is associated with a dosage effect of the putative ribosome-associated protein D-p40 on spineless. *Genetics*, 135, 553-564.

Ouzonis, C., Kyrpides, N. and Sander, C. (1995) Novel protein families in archaean genomes. *Nucleic Acids Res*, 23, 565-570.

Pelegrin, M., Marin, M., Noel, D., Del Rio, M., Saller, R., Stange, J., Mitzner, S., Gunzburg, W. H. and Piechaczyk, M. (1998) Systemic long-term delivery of antibodies in immunocompetent animals using cellulose sulphate capsules containing antibody-producing cells. *Gene Ther*, 5, 828-834.

Pelegrin, M., Marin, M., Oates, A., Noel, D., Saller, R., Salmons, B. and Piechaczyk, M. (2000) Immunotherapy of a viral disease by in vivo production of therapeutic monoclonal antibodies. *Hum Gene Ther*, 11, 1407-1415.

Prusiner, S. B., Scott, M. R., DeArmond, S. J. and Cohen, F. E. (1998) Prion protein biology. *Cell*, 93, 337-348.

Rao, C. N., Castronovo, V., Schmitt, M. C., Wewer, U. M., Claysmith, A. P., Liotta, L. A. and Sobel, M. E. (1989) Evidence for a precursor of the high-affinity metastasis-associated murine laminin receptor. *Biochemistry*, 28, 7476-7486.

Rao, N. C., Barsky, S. H., Terranova, V. P. and Liotta, L. A. (1983) Isolation of a tumor cell laminin receptor. *Biochem. Biophys. Res. Commun.*, 111, 804-808.

Rieger, R., Edenhofer, F., Lasmézas, C. I. and Weiss, S. (1997) The human 37-kDa laminin receptor precursor interacts with the prion protein in eukaryotic cells. *Nat Med*, 3, 1383-1388.

Rieger, R., Lasmezas, C. I. and Weiss, S. (1999) Role of the 37 kDa laminin receptor precursor in the life cycle of prions. *Transfus Clin Biol*, 6, 7-16.

Rohrer, J. W., Barsoum, A. L. and Coggin, J. H., Jr. (2001) The Development of a New Universal Tumor Rejection Antigen expressed on Human and Rodent Cancers for Vaccination, Prevention of Cancer, and Anti-Tumor Therapy. *Mod Asp Immunobiol*, 1, 191-195.

Rosenthal, E. T. and Wordeman, L. (1995) A protein similar to the 67 kDa laminin binding protein and p40 is probably a component of the translational machinery in Urechis caupo oocytes and embryos. *J. Cell. Sci.*, 108, 245-256.

Salas, P. J., Ponce, M. I., Brignoni, M. and Rodriguez, M. L. (1992) Attachment of Madin-Darby canine kidney cells to extracellular matrix: role of a laminin binding protein related to the 37/67 kDa laminin receptor in the development of plasma membrane polarization. *Biol Cell*, 75, 197-210.

Sato, M., Kinoshita, K., Kaneda, Y., Saeki, Y., Iwamatsu, A. and Tanaka, K. (1996) Analysis of nuclear localization of laminin binding protein precursor p40 (LBP/p40). *Biochem Biophys Res Commun*, 229, 896-901.

Sato, M., Saeki, Y., Tanaka, K. and Kaneda, Y. (1999) Ribosome-associated protein LBP/p40 binds to S21 protein of 40S ribosome: analysis using a yeast two-hybrid system. *Biochem Biophys Res Commun*, 256, 385-390.

Stephenson, D. A., Chiotti, K., Ebeling, C., Groth, D., DeArmond, S. J., Prusiner, S. B. and Carlson, G. A. (2000) Quantitative trait loci affecting prion incubation time in mice. *Genomics*, 69, 47-53.

Wang, K. S., Kuhn, R. J., Strauss, E. G., Ou, S. and Strauss, J. H. (1992) High-affinity laminin receptor is a receptor for Sindbis virus in mammalian cells. *J Virol*, 66, 4992-5001.

Wewer, U. M., Liotta, L., Jaye, M., Ricca, G. A., Drohan, W. N., Claysmith, A. P., Rao, C. N., Wirth, P., Coligan, J. E., Albrechtsen, R., Mudry, M. and Sobel, M. E. (1986) Altered levels of laminin receptor mRNA in various human carcinoma cells that have different abilities to bind laminin. *Proc. Natl. Acad. Sci. USA*, 83, 7137-7141.

Yow, H., Wong, J. M., Chen, H. S., Lee, C., Steele, G. D. J. and Chen, L. B. (1988) Increased mRNA expression of a laminin-binding protein in human colon carcinoma: complete sequence of a full-length cDNA encoding the protein. *Proc. Natl. Acad. Sci. USA*, 85, 6394-6398.

The invention claimed is:

1. A single-chain antibody molecule, which is directed specifically against laminin receptor precursor (LRP)/laminin receptor (LR), and which comprises amino acid sequence SEQ ID NO: 2.

2. A single-chain antibody molecule, which is directed specifically against LRP/LR, and which comprises amino acid sequence SEQ ID NO: 4.

3. The antibody molecule as claimed in claim 1 or 2, wherein a c-myc tag is inserted between $V_L$ domain and hexahistidine tag.

4. A process for producing an antibody molecule as claimed in one of claims 1 and 2, which comprises culturing host cells comprising a cDNA comprising nucleotide sequence SEQ IDNO: 1 or SEQ ID NO: 3 carried by a replication or expression vector which is a recombinant adeno-associated virus (AAV), under conditions effective for expression of an antibody molecule.

5. A diagnostic composition which comprises an antibody molecule according to one of claims 1 and 2 in combination with an acceptable diluent and/or vehicle.

6. The diagnostic composition as claimed in claim 5, which is suitable for detection in body fluids.

7. The diagnostic composition as claimed in claim 6, wherein the body fluids are blood or cerebrospinal fluid.

8. The diagnostic composition as claimed in claim 5, which is suitable for detection in tissues.

9. The diagnostic composition as claimed in claim 8, wherein the tissues are brain tissue.

10. The diagnostic composition as claimed in claim 8, wherein the tissues are lymphatic tissue.

11. The diagnostic composition as claimed in claim 5, which is suitable for detection of malignant degeneration (cancer)

12. The diagnostic composition as claimed in claim 11, wherein the detection is carried out in body fluids.

13. The diagnostic composition as claimed in claim 12, wherein the body fluids are blood or cerebrospinal fluid.

14. The diagnostic composition as claimed in claim 11, wherein the detection is carried out in tissues.

* * * * *